(12) United States Patent
Gross et al.

(10) Patent No.: US 8,557,169 B2
(45) Date of Patent: Oct. 15, 2013

(54) PROCESS FOR MAKING AN EMBOSSED WEB

(75) Inventors: Sarah Beth Gross, Harrison, OH (US); Richard George Coe, Cincinnati, OH (US); Gary Wayne Gilbertson, Fairfield, OH (US); Keith Joseph Stone, Fairfield, OH (US); Roger Dale Young, Fort Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 362 days.

(21) Appl. No.: 12/879,567

(22) Filed: Sep. 10, 2010

(65) Prior Publication Data

US 2011/0221094 A1 Sep. 15, 2011

Related U.S. Application Data

(63) Continuation-in-part of application No. 12/722,020, filed on Mar. 11, 2010, and a continuation-in-part of application No. 12/721,989, filed on Mar. 11, 2010, and a continuation-in-part of application No. 12/722,002, filed on Mar. 11, 2010, and a continuation-in-part of application No. 12/721,868, filed on Mar. 11, 2010, now Pat. No. 8,206,628.

(51) Int. Cl.
*B29C 59/02* (2006.01)

(52) U.S. Cl.
USPC ............ 264/504; 264/285; 264/286; 264/503; 264/508; 264/555; 264/570

(58) Field of Classification Search
USPC .......... 264/285, 286, 503, 504, 508, 555, 570
See application file for complete search history.

(56) References Cited

U.S. PATENT DOCUMENTS

| | | |
|---|---|---|
| 3,600,361 A | 8/1971 | Heacock et al. |
| 3,719,736 A | 3/1973 | Woodruff |

(Continued)

FOREIGN PATENT DOCUMENTS

| | | |
|---|---|---|
| DE | 34 39 555 A1 | 4/1986 |
| EP | 0 598 970 | 6/1994 |

(Continued)

OTHER PUBLICATIONS http://en.wikipedia.org/wiki/Cellulose (retrieved Jan. 11, 2013).*

(Continued)

*Primary Examiner* — Timothy Kennedy
(74) *Attorney, Agent, or Firm* — Andrew J. Mueller; Amanda T. Barry

(57) ABSTRACT

A process for making an embossed web includes providing a precursor web a first forming structure having a plurality of discrete first forming elements and a first pressure source and applying pressure between the first pressure source and the first forming structure to force the precursor web to conform to the first forming elements of to form a first embossed web having a plurality of first discrete extended elements. The first embossed web is then provided between a second forming structure having a plurality of discrete second forming elements and a second pressure source and pressure is applied between the second pressure source and the second forming structure to force the first embossed web to conform to the second forming elements to form a second embossed web having a plurality of second discrete extended elements. The resulting embossed web has a plurality of first and second discrete extended elements.

20 Claims, 10 Drawing Sheets

(56) References Cited

U.S. PATENT DOCUMENTS

| | | | |
|---|---|---|---|
| 3,750,508 A | | 8/1973 | Miles |
| 3,779,285 A | | 12/1973 | Sinibaldo |
| 3,911,187 A | * | 10/1975 | Raley .................... 264/284 |
| 4,211,743 A | | 7/1980 | Kos et al. |
| 4,319,868 A | | 3/1982 | Riemersma et al. |
| 4,343,848 A | | 8/1982 | Leonard, Jr. |
| 4,546,029 A | | 10/1985 | Cancio et al. |
| 4,695,422 A | * | 9/1987 | Curro et al. .................. 264/504 |
| 4,778,644 A | | 10/1988 | Curro et al. |
| 5,158,819 A | | 10/1992 | Goodman et al. |
| 5,281,371 A | | 1/1994 | Tamura et al. |
| 5,650,215 A | | 7/1997 | Mazurek et al. |
| 5,670,110 A | | 9/1997 | Dirk et al. |
| 5,709,829 A | | 1/1998 | Giacometti |
| 5,783,014 A | | 7/1998 | Biogioli et al. |
| 5,814,389 A | | 9/1998 | Giacometti |
| 5,858,515 A | | 1/1999 | Stokes et al. |
| 5,945,196 A | | 8/1999 | Ricker et al. |
| 5,972,280 A | | 10/1999 | Hoagland |
| 6,007,468 A | | 12/1999 | Giacometti |
| H1927 H | | 12/2000 | Chen et al. |
| 6,228,462 B1 | | 5/2001 | Lee |
| 6,368,539 B1 | | 4/2002 | Greenfield |
| 6,599,612 B1 | | 7/2003 | Gray |
| 6,719,742 B1 | | 4/2004 | McCormack et al. |
| 6,846,445 B2 | | 1/2005 | Kim et al. |
| 7,037,569 B2 | | 5/2006 | Curro et al. |
| 7,297,226 B2 | * | 11/2007 | Schulz .................... 162/117 |
| 7,402,723 B2 | | 7/2008 | Stone et al. |
| 7,642,207 B2 | | 1/2010 | Bohemer et al. |
| 7,799,254 B2 | | 9/2010 | Harvey et al. |
| 2001/0014796 A1 | | 8/2001 | Mizutani et al. |
| 2003/0187170 A1 | | 10/2003 | Burmeister |
| 2003/0201582 A1 | * | 10/2003 | Gray .................... 264/504 |
| 2003/0228445 A1 | | 12/2003 | Vaughn et al. |
| 2004/0046290 A1 | | 3/2004 | Kim et al. |
| 2004/0122395 A1 | | 6/2004 | Stone et al. |
| 2004/0131820 A1 | | 7/2004 | Turner et al. |
| 2004/0161586 A1 | | 8/2004 | Cree et al. |
| 2004/0209041 A1 | * | 10/2004 | Muth et al. .................. 428/131 |
| 2005/0191496 A1 | | 9/2005 | Gray et al. |
| 2005/0279470 A1 | | 12/2005 | Redd et al. |
| 2006/0087053 A1 | | 4/2006 | O'Donnell et al. |
| 2006/0286343 A1 | | 12/2006 | Curro et al. |
| 2007/0062658 A1 | | 3/2007 | Wiwi et al. |
| 2007/0144693 A1 | | 6/2007 | Ruthven |
| 2007/0261224 A1 | | 11/2007 | McLeod |
| 2008/0200320 A1 | | 8/2008 | Buckner et al. |
| 2008/0264275 A1 | | 10/2008 | Wilhelm et al. |

FOREIGN PATENT DOCUMENTS

| | | |
|---|---|---|
| GB | 1 344 054 A | 1/1974 |
| GB | 1344054 A | 1/1974 |
| WO | WO-97/13633 | 4/1997 |
| WO | WO 97/13633 A1 | 4/1997 |
| WO | WO 2008/120959 A1 | 10/2008 |
| WO | WO 2008-120959 A1 | 10/2008 |

OTHER PUBLICATIONS

PCT International Search Report dated Dec. 22, 2010.

Nagarajan, Abbott, Yao; Rubber-Assisted Embossing Process; School of Polymer, Textile & Fiber Eng., Georgia Institute of Technology, Atlanta, GA 30332; ANTEC (2007) vol. 5, pp. 2921-2925, 5 pages.

Chang, Yang; Gas pressurized hot embossing for transcription of micro-features; Microsystem Technologies (2003) vol. 10 pp. 76-80 5 pages; Springer-Verlag.

Dreuth Heiden; Thermoplastic strucuring of thin polymer films; Sensors and Actuators (1999) vol. 78 pp. 198-204, 7 pages; Institute of Applied Physics, University of Giessen, Heinrich-Buff-Ring 16 D-35392 Giessen, Germany; Elsevier Sciences S.A.

Heckele, Schomburg; Review on micro molding of thermoplastic polymers; Institute of Physics Publishing; Journal of Micromechanics and Microengineering (2004) vol. 14, No. 3, pp. R1-R14, 14 pages; IOP Publishing Ltd.

Kimerling, Liu, Kim, Yao; Rapid hot embossing of polymer microfeatures; Microsystem Technologies (2006) vol. 12, No. 8, pp. 730-735, 6 pages; School of Polymer, Textile and Fiber Eng., Georgia Institute of Technology, Atlanta GA 30332.

Nagarajan, Yao, Ellis, Azadegan; Through-Thickness Embossing Process for Fabrication of Three-Dimensional Thermoplastic Parts; School of Polymer, Textile & Fiber Eng., Georgia Institute of Technology Atlanta GA 30332 and Delphi Research Labs, Shelby Township, Michigan 48315; Polymer Engineering and Science (2007) vol. 47, No. 12, pp. 2075-2084, 10 pages.

Rowland, King; Polymer deformation and filling modes during microembossing; Woodruff School of Mechanical Engineering, Georgia Institute of Technology, Atlanta, GA 30329-0405; Institute of Physics Publishing; Journal of Micromechanics and Microengineering (2004) vol. 14, No. 12, pp. 1625-1632, 8 pages; IOP Publishing Ltd.

Truckenmuller, Giselbrecht; Microthermoforming of flexible, not-buried hollow microstructures for chip-based life sciences applications; IEE Proceedings—Nanobiotechnology (Aug. 2004) Vol, 151, No. 4, pp, 163-166; 4 pages.

Yao, Nagarajan; Cold Forging Method for Polymer Microfabrication; Department of Mechanical Engineering, Oakland University, Rochester, MI 48309; Polymer Engineering and Science (Oct. 2004) vol. 44, No, 10, pp. 1998-2004, 7 pages.

Yao, Nagarajan, Li, Yi; A Two-Station Embossing Process for Rapid Fabrication of Surface Microstructures on Thermoplastic Polymers; School of Polymer, Textile & Fiber Eng., Georgia Institute of Technology, Atlanta, GA 30332 and Department of Industrial, Welding and Systems Engineering, The Ohio State University, Columbus, OH 43210; Polymer Engineering and Science (2007) vol. 47, No. 4, pp. 530-539, 10 pages; Wiley InterScience; Society of Plastics Engineers.

Yao, Kuduva-Raman-Thanumoorthy; An enlarged process window for hot embossing; School of Polymer, Textile & Fiber Eng., Georgia Institute of Technology Atlanta, GA 30332; Journal of Micromechanics and Microengineering (2008) vol. 18, pp. 1-7; 7 pages; IOP Publishing Ltd.

* cited by examiner

PROCESS FOR MAKING AN EMBOSSED WEB

CROSS REFERENCE TO RELATED APPLICATION

This application is a continuation-in-part application of U.S. patent application Ser. Nos. 12/722,020, 12/721,989, 12/722,002, and 12/721,868 now U.S. Pat. No. 8,206,628, each filed on Mar. 11, 2010, the disclosures of which are incorporated herein by reference in their entireties.

FIELD OF THE INVENTION

The invention relates to a process for making an embossed web comprising a plurality of discrete extended elements.

BACKGROUND OF THE INVENTION

Web materials, such as thermoplastic films, have a variety of uses including component materials of absorbent articles (such as topsheets and backsheets), packaging (such as flow wrap, shrink wrap, and polybags), trash bags, food wrap, dental floss, wipes, electronic components, and the like. For many of these uses of web materials, it can be beneficial for the web material to have a textured surface which can provide the surface of the web material with a desirable feel, visual impression, and/or audible impression.

Polymeric webs exhibiting a soft and silky tactile impression can be made via a vacuum forming process or a hydroforming process. With a typical vacuum forming process, a precursor web is heated and placed over a forming structure. Then a vacuum forces the precursor web to conform to the texture of the forming structure. The resulting polymeric web has texture that can provide a soft and silky tactile impression, depending upon the texture of the forming structure and degree of conformation. While a vacuum forming process can be suitable for making a soft and silky polymeric web, a vacuum forming process is typically limited with respect to the amount of pressure capable of being exerted onto a precursor web. As a result, it is usually required to heat a precursor film to significantly soften or melt the precursor film prior to placement on the forming structure in order to vacuum form the precursor film to the forming structure. A vacuum forming process is therefore an inefficient process in terms of how fast the process can be performed due to the heating step and the limited pressures generated by the process.

With a typical hydroforming process, a precursor web is placed over a forming structure and high pressure and high temperature water jets force the precursor web to conform to the texture of the forming structure. The resulting polymeric web can have texture that can provide a soft and silky tactile impression, depending upon the texture of the forming structure. A hydroforming process, although capable of producing soft and silky polymeric webs, is typically a costly and inefficient process involving the use of high pressure and high temperature water jets and subsequent drying steps, including dewatering steps.

Embossing is a process that typically involves the act of mechanically working a substrate to cause the substrate to conform under pressure to the depths and contours of a pattern engraved or otherwise formed on an embossing roll. It is widely used in the production of consumer goods. Manufacturers use the embossing process to impart a texture or relief pattern into products made of textiles, paper, synthetic materials, plastic materials, metals, and wood.

Embossing processes have been used to provide texture to polymeric films. However, such embossing processes typically require extruding a molten resin onto a forming structure or heating a precursor web before placement onto a forming structure and then embossing to produce an embossed web. The embossed web is then cooled, typically by cooling the embossing rolls or plates used to emboss the heated precursor web or molten resin. The cooling step is often utilized to set the texture in the embossed web. However, these heating and cooling steps add undesirable cost and inefficiency, as well as complexity, to the process. In addition, such embossing processes typically involve relatively large dwell times, which can result in slow, inefficient processes.

It is also typically difficult to impart relatively small scale texture to precursor webs using conventional embossing processes. Furthermore, typical embossing processes tend to produce embossed webs having relatively uniform thickness throughout the web.

For example, U.S. Pat. No. 5,972,280 discloses an embossing process utilizing a hot engraved surface of an embossing roll and static pressure applied within a chamber to heat a web and deform it over the surface of the embossed roll. This process uses elevated temperatures, which are typically above the softening temperature of the web, and relatively low pressures of about 0.007 MPa to about 0.7 MPa. As a result, the embossed pattern is formed as indentations disposed on only a single surface of the web, without affecting the opposite surface of the web.

Despite the knowledge in the art, there remains a desire to develop a more efficient process for making embossed webs that have desirable feel, visual impression, and/or audible impression, especially embossed webs exhibiting thinning in desirable areas of the embossed web. In certain aspects, a desired process is efficient with respect to the energy and resources required by the process. In certain aspects, a desired process is capable of running at high speeds. In certain aspects, a desired process is capable of running at relatively low temperatures, such as ambient temperature.

SUMMARY OF THE INVENTION

In one embodiment, a process for making an embossed web includes feeding a precursor web between a first pressure source and a first forming structure includes a plurality of first forming elements, and applying pressure from the first pressure source against the precursor web opposite the first forming structure creating a pressure differential across the precursor web sufficient to conform the precursor web to the first forming elements of the first forming structure, thereby forming a first embossed web that includes a plurality of first discrete extended elements having open proximal ends. The process further includes feeding the first embossed web between a second pressure source and a second forming structure that includes a plurality of second forming elements, and applying pressure from the second pressure source against the first embossed web opposite the second forming structure creating a pressure differential across the first embossed web sufficient to conform the first embossed web to the second forming elements of the second forming structure, thereby forming a second embossed web that includes a plurality of second discrete extended having open proximal ends. The first and second forming elements are selected from the group consisting of discrete protruded elements, discrete apertures, discrete depressions, and combinations thereof. The discrete protruded elements having a height and the discrete apertures and discrete depressions having a depth, the height and the depth being at least substantially equal to a thickness of the precursor web. The first and second pressure sources are selected from the group consisting of static gas pressure plenums and compliant substrates

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
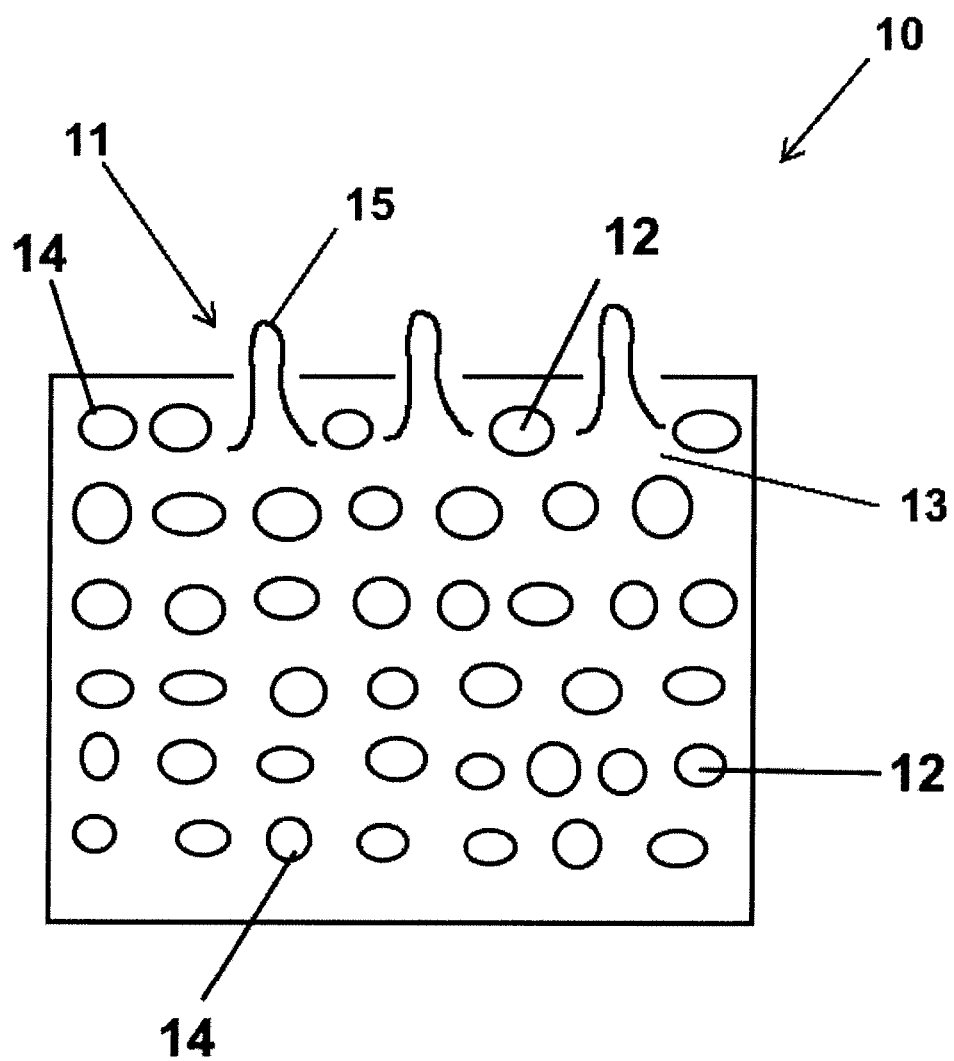
FIG. 1 is a top view of a forming structure in accordance with an embodiment of the disclosure.

Disclosed herein is a process for forming an embossed web that overcomes one or more of the aforementioned shortcomings of the prior art. Specifically, embodiments of the process now make possible a more efficient web embossing process. For example, embodiments of the process can now make possible the ability to impart relatively small scale texture to webs. Furthermore, embodiments of the process can now make possible the ability to avoid the cumbersome heating and cooling steps that the prior art required. Still further, embodiments of the process do not require the large dwell times required of prior art processes. Additionally, as compared to prior art static pressure processes, embodiments of the process can allow for the formation of three-dimensional discrete extended elements having open proximal ends and open or closed distal ends. Embodiments of the process can also allow for lower cost, more durable forming structures to be used. In certain embodiments, the process can be used to form macro-scale structures for use, for example, as packaging materials such as bubble wrap.

The process generally includes a first embossing step in which a precursor web is fed between a first pressure source and a first forming structure comprising a plurality of discrete first forming elements. The discrete first forming elements can include, for example, discrete protruded elements, discrete apertures, discrete depressions, or combinations thereof. The process further includes applying pressure from the first pressure source against the precursor web and the first forming structure sufficient to conform the precursor web to the discrete forming elements of the first forming structure, thereby forming a first embossed web. The first pressure source can either be a static pressure plenum or a compliant substrate. The first embossed web includes a plurality of first discrete extended elements having open proximal ends.

The process also includes a second embossing step in which the first embossed web is fed between a second pressure source and a second forming structure comprising a plurality of discrete second forming elements. The discrete second forming elements can include, for example, discrete protruded elements, discrete apertures, discrete depressions, or combinations thereof. The process includes applying pressure from the second pressure source against the first embossed web and the second forming structure sufficient to conform the first embossed web to the discrete second forming elements of the second forming structure, to thereby form a second embossed web. The second pressure source can either be a static pressure plenum or a compliant substrate. The second embossed web includes a plurality of second discrete extended elements having open proximal ends. The second embossed web also includes the plurality of first discrete extended elements.

The process can further include any additional number of embossing steps in which the resulting embossed web from the previously performed embossing step is fed between a pressure source and a forming structure comprising a plurality of forming elements and pressure is applied from the second pressure source against the embossed web and the forming structure sufficient to conform the embossed web to the discrete forming elements of the forming structure. These aspects of the process are described in further detail below.

Advantageously, the process disclosed herein can allow for use of forming structures having wider edge-to-edge spacing between adjacent forming elements as well as a lower area density of forming elements, while producing embossed webs having smaller sale spacing between adjacent discrete extended elements and a high density of discrete extended elements such as would be produced by a single forming structure having a small edge-to-edge spacing between adjacent forming elements and a high density of forming elements. Such forming structures having fewer forming elements and wider spacing between adjacent elements are cheaper and easier to manufacture and have significantly increased life span as compared to forming structures having a higher area density of forming elements with narrower spacing between adjacent elements. In addition, when a compliant substrate is used, a sizable increase in substrate lifetime can be observed when using such a forming structure. While not being bound by theory, it is believed that the increase in lifetime is due to the reduction in tensile stresses on the compliant substrate as it is being forced down between adjacent protruded elements. For example, a $10^4$ times increase in lifespan of a compliant substrate can be achieved by increasing the edge-to-edge spacing between adjacent forming elements from about 250 μm to about 400 μm. When a gas pressure plenum is used, lower pressures can be used as the edge-to-edge distance is increased.

Forming Structure

Referring to FIGS. 1 and 2, a forming structure 10 useful as the first and/or second forming structures 10A, 10B in the process of the present disclosure includes a plurality of discrete forming elements 11. As used herein, "forming structure 10" refers generally to the first and/or second forming structures 10A, 10B as well as any additional forming structures 10 of additional embossing steps. The first and second forming structures 10A, 10B can have, for example, the same type of forming elements 11. For example, both the first and second forming structures 10A, 10B can include discrete protruded elements 15. In various embodiments, the first and second forming structures 10A, 10B can have the same type of forming elements 11 and the forming elements 11 of each forming structure 10 can have substantially the same or different shapes, sizes, aspect ratios, and/or edge-to-edge spacing. Alternatively, the first and second forming structures 10A, 10B can have different forming elements 11. For example, the first forming structure 10A can include discrete apertures 12 while the second forming structure 10B includes discrete protruded elements 15. In yet another embodiment of the method, the first and second forming structures 10A, 10B can be the same forming structure, such that only a single forming structure is used when pressure is applied from the first and the second pressure sources. Any combination of forming elements 11 can be used on the first and second forming structures 10A, 10B.

The discrete forming elements 11 of either or both of the first and second forming structures 10A, 10B can include, discrete protruded elements 15, discrete apertures 12, discrete depressions 14, or a combination thereof. The forming structure 10 can further include lands completely surrounding the discrete forming elements 11. The discrete forming elements 11 of the forming structure 10 can be small in scale relative to typical patterns used on forming structures 10 in conventional embossing processes. The process of the disclosure can produce embossed webs 16 that include relatively high aspect ratio extended elements 11 with thinned distal ends 24 and/or sidewalls, even without heating webs and even at high speeds.

Figure 2A:
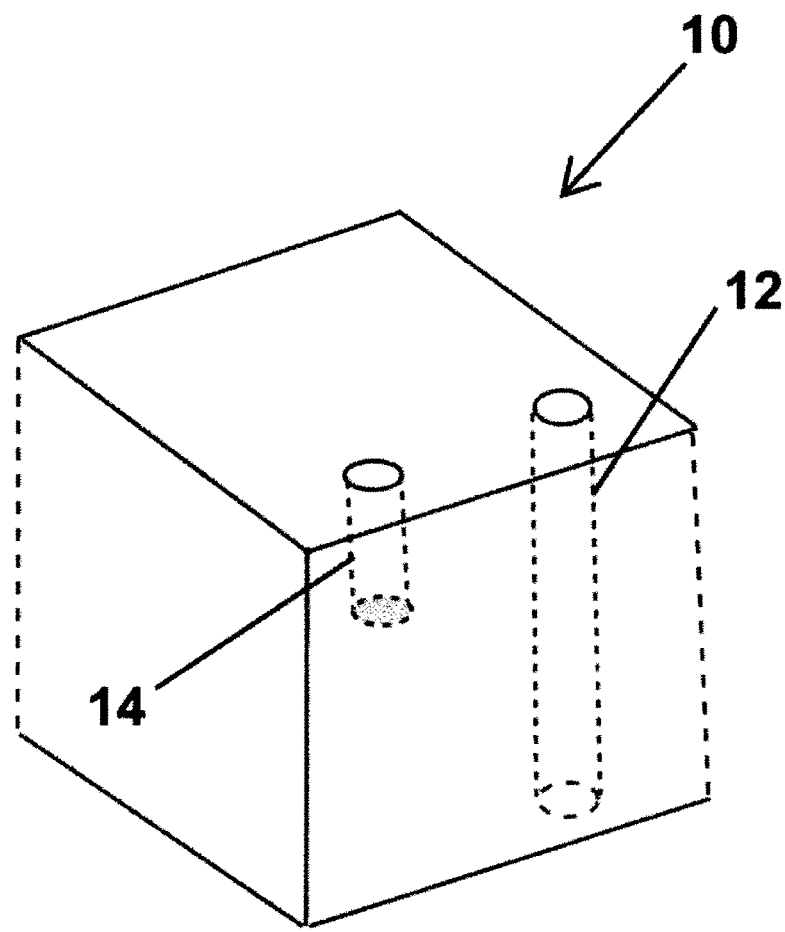
FIG. 2A is a perspective view of a forming structure in accordance with an embodiment of the disclosure illustrating the distinction between apertures and depressions.

FIG. 2A illustrates the distinction between apertures 12 and depressions 14. As used herein, "apertures 12" refers to an opening in the forming structure 10 that does not include a bottom surface limiting the depth of the opening. In contrast, as used herein, "depressions 14" refers to an opening in the forming structure 10 having a bottom surface limiting the depth of the opening to be less than the thickness of the forming structure 10. The bottom surface can be, for example, porous or non-porous. For example, the bottom surface can include an opening, having a width smaller than the diameter of the depression 14, that vents the depression 14 by allowing air to pass through the depression 14. In one embodiment, the forming structure 10 has a means to allow any air trapped under the web to escape. For example, a vacuum assist can be provided to remove the air under the web so as not to increase the required compliant pressure. The bottom surface can be flat, rounded, or sharp. The forming structure 10 can be a solid roll, or have a thickness of about 25 microns to about 5000 microns, or about 100 microns to about 3000 microns. The apertures 12 and depressions 14 can have a depth of about 10 microns to about 500 microns, or about 25 microns to about 5000 microns. As used herein, the depth of the aperture 12 corresponds to the thickness of the forming structure 10 because the aperture 12 has no bottom surface limiting its depth. In one embodiment the apertures 12 and depressions 14 can have a depth substantially equal to the thickness of at least one of the webs, at least twice the thickness of at least one of the webs, or at least three times the thickness of at least one of the webs. Preferably, the apertures 12 and depressions 14 have a depth that is at least three times the total thickness of the webs.

The perimeter of the apertures 12 or depressions 14 on the web contacting surface of the forming structure 10 can have a straight edge or can have a radius of curvature as measured from the web contacting surface of the forming structure 10 into the aperture 12 or depression 14. The radius of curvature can be about 0 microns to about 2000 microns, preferably about 0 microns to about 25 microns, and more preferably about 2 microns to about 25 microns. In one embodiment, an angled taper, commonly known as a chamfer, is used. In one embodiment a combination of straight edges and radii are used.

The apertures 12 or depressions 14 have a diameter, which for a generally cylindrical structure is the inside diameter. For non-uniform cross-sections, and/or non-cylindrical structures of apertures 12 or depressions 14, diameter is measured as the average cross-sectional dimension of apertures 12 or depressions 14 at the top surface of the forming structure 10. Each aperture 12 or depression 14 can have diameter of about 40 microns to about 2,000 microns. Other suitable diameters include, for example, about 50 microns to about 500 microns, about 65 microns to about 300 microns, about 75 microns to about 200 microns, about 10 microns to about 5000 microns, about 50 microns to about 5000 microns, about 500 microns to about 5000 microns, or about 800 microns to about 2,500 microns.

In one embodiment, the diameter of apertures 12 or depressions 14 is constant or decreases with increasing depth. In another embodiment, the diameter of the apertures 12 or depressions 14 increases with increasing depth. For example, the discrete apertures 12 or depressions 14 can have a first diameter at a first depth and a second diameter at a second depth deeper than the first depth. For example, the first diameter can be larger than the second diameter. For example, the second diameter can be larger than the first diameter.

The sidewalls of the discrete apertures 12 or depressions 14 can be completely vertical or can be tapered. In one embodiment, the discrete apertures 12 or depressions 14 have tapered sidewalls. This can allow the web to more easily separate from the forming structure 10 after embossing. In one embodiment, the sidewalls will typically have a degree of taper of about 0° to about −50° to about 50°, about −30° to about 30°, about 0° to about 50°, about 2° to about 30°, or about 5° to about 25°.

Figure 2B:
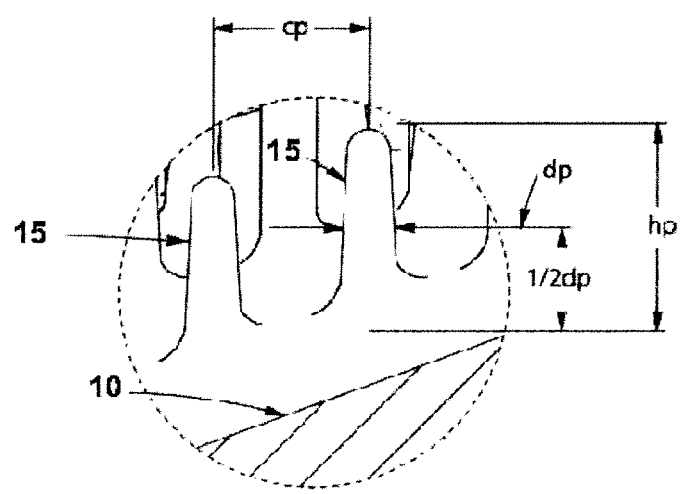
FIG. 2B is an enlarged perspective view of a portion of the forming structure having discrete protruded elements.

The discrete protruded elements 15 can have a height of at least about 50 microns, at least about 75 microns, at least about 100 microns, at least about 150 microns, at least about 250 microns, or at least about 380 microns. The discrete protruded elements 15 can have a diameter, which for a generally cylindrical structure is the outside diameter. For non-uniform cross-sections, and/or non-cylindrical structures of protruded elements 15, diameter dp is measured as the average cross-sectional dimension of protruded elements 15 at ½ the height hp of the protruded elements 15, as shown in FIG. 2B. The discrete protruded elements 15 can have diameter dp that can be from about 10 microns to about 5,000 microns, about 50 microns to about 5,000 microns, about 50 microns to about 3,000 microns, about 50 microns to about 500 microns, about 65 microns to about 300 microns, or about 75 microns to about 200 microns. In one embodiment, the discrete protruded elements 15 of the forming structure 10 will have a diameter of less than about 500 microns. In addition, in certain embodiments, the discrete protruded elements 15 can have larger diameters d up to about 2.5 centimeters, up to about 2 centimeters, up to about 1.5 centimeters, up to about 1 cm, up to about 0.5 centimeters, or up to about 0.1 centimeters.

For each protruded element 15, a protruded element aspect ratio, defined as hp/dp, can be determined Protruded elements 15 can have an aspect ratio hp/dp of at least about 0.5, at least about 0.75, at least about 1, at least about 1.5, at least about 2, at least about 2.5, or at least about 3 or higher. In general, because the actual height hp of each individual protruded element 15 may vary, an average height ("hpavg") of a plurality of protruded elements 15 can be determined by determining a protruded element average minimum amplitude ("Apmin") and a protruded element average maximum amplitude ("Apmax") over a predetermined area of forming structure 10. Likewise, for varying cross-sectional dimensions, an average protrusion diameter ("dpavg") can be determined for a plurality of protrusions 15. Such amplitude and other dimensional measurements can be made by any method known in the art, such as by computer aided scanning microscopy and related data processing. Therefore, an average aspect ratio of the protruded elements 15, ("ARpavg") for a predetermined portion of the forming structure 10 can be expressed as hpavg//dpavg.

The discrete protruded elements 15 of the forming structure 10 can have distal ends 24 that are flat, rounded or sharp, depending upon whether it is desired to produce an embossed web 16 having discrete extended elements 22 with distal ends 24 that are open (requiring a sharper protruded element on the forming structure 10) or closed (requiring a more rounded protruded element on the forming structure 10). The rounded distal ends 24 of the discrete protruded elements 15 of the forming structure 10 can have a certain tip radius, such as from about 5 microns to about 150 microns, from about 10 microns to about 100 microns, from about 20 to about 75 microns, or from about 30 microns to about 60 microns.

The sidewalls of the discrete protruded elements 15 can be completely vertical or can be tapered. In one embodiment, the discrete protruded elements 15 have tapered sidewalls, as tapered sidewalls can have an impact on durability and longevity of the pressure source. For example, the tapered sidewalls can ease the compression or tension on compliant substrate 44 as it conforms around discrete forming elements 11 of the forming structure 10. This can also allow the web to more easily separate from the forming structure 10 after embossing. In one embodiment, the sidewalls will typically have a degree of taper of from about 0° to about 50°, from about 2° to about 30°, or from about 5° to about 25°.

In one embodiment, the protruded elements 15 can be spherical, ellipsoid, or snowman-shaped, having different or varying diameters along the height of the protruded element.

In one embodiment, the forming elements 11 of a single forming structure 10 can have varying geometries, such as height of the protruded elements 15 and depth of the apertures 12 or depressions 14 For example, the forming elements 11 can gradually increase in height or over a range of tens or hundreds of adjacent protruded elements 15, which can result in the web having discrete extended elements 22 with varying heights Other features of the forming structure 10 which results in corresponding features of the discrete extended elements 22 can be adjusted to form gradient characteristic in the discrete extended elements 22 of the embossed web 16.

For example, the forming structure 10 can include an area density gradient of forming elements 11.

The discrete forming elements 11 of the forming structure 10 can have a variety of different cross-sectional shapes, such as generally columnar or non-columnar shapes, including circular, oval, hour-glass shaped, star shaped, polygonal, and the like, and combinations thereof. Polygonal cross-sectional shapes include, but are not limited to, rectangular, triangular, hexagonal, or trapezoidal. In one embodiment, the discrete depressions 14 can have a length substantially equal to the length of the forming structure 10 so as to form grooves about substantially the entire length of the forming structure 10.

In general, the forming structure 10, for a given portion of thereof, will include at least about 4 discrete forming elements 11 per square centimeter, at least about 10 discrete forming elements 11 per square centimeter, at least about 95 discrete forming 11 per square centimeter, at least about 240 discrete forming elements 11 per square centimeter, about 350 to about 10,000 discrete forming elements 11 per square centimeter, about 500 to about 5,000 discrete forming elements 11 per square centimeter, or about 700 to about 3,000 discrete forming elements 11 per square centimeter.

The discrete forming elements 11 can have an average edge-to-edge spacing between two adjacent discrete forming elements 11 of about 30 microns to about 1000 microns, about 50 microns to about 800 microns, about 150 microns to about 600 microns, or about 180 microns to about 500 microns. The edge-to-edge spacing of the adjacent forming elements 11 of the first and second forming structures 10A, 10B can be controlled so as to control the spacing of the resulting first and second discrete extended elements 22A, 22B. For example, the discrete second forming elements 11B of the second forming structure 10B can be spaced a specified distance such that, for example, the resulting second discrete extended elements 22B are formed halfway between the adjacent first discrete extended elements 22A formed by the first embossing process using the first forming structure 10A.

In certain embodiments, a portion (or area) of the forming structure 10 can include area densities of discrete forming elements 11 as described in the preceding paragraph, while other portions (or areas) of the forming structure 10 may include no discrete forming elements 11. The areas of the forming structure 10 having no discrete forming elements 11 can be located in a different horizontal plane. In other embodiments, the discrete forming elements 11 of the forming structure 10 can be located in different horizontal planes of the forming structure 10. The regions having no discrete forming elements 11 and/or the regions having discrete forming elements 11 located in different horizontal planes of the forming structure 10 can be in the form of a specific pattern or design, such as a flower, bird, ribbon, wave, cartoon character, logo, and the like, so that the embossed web 16 will have a region that stands out visually from, and/or has a different hand feel when touched relative to, the remainder of the web. For example, the embossed web 16 can include a non-embossed region that stands out visually from, and/or has a different hand feel from embossed regions. U.S. Pat. No. 5,158,819 provides suitable examples of forming structures 10 for use in these embodiments.

The discrete forming elements 11 of the first and second forming structures 10A, 10B can be arranged in any suitable manner. For example, each of the first and second forming structures 10A, 10B can include portions of the forming structures 10 containing no discrete forming elements 11. The portions of the forming structures 10 not containing discrete forming elements 11 can be aligned or can be offset. In one embodiment, each of the first and second forming structures 10A, 10B includes a portion having no discrete forming elements 11 in the form of a pattern or design and the portion of the second forming structure 10B having no discrete forming elements 11 is offset from the portion of the first forming structure 10A having no discrete forming element such that a shadow effect in the pattern is created when a precursor web 34 is embossed in two embossing processes using the first and second forming structures 10A, 10B. Alternatively, a shadow effect of the pattern can be created using first and second forming structures 10A, 10B having aligned portions having no discrete forming elements 11 and controlling the location of the first embossed web 16A when it is fed between the second forming structure 10B and the second pressure source.

In one embodiment, a ratio of the average depth of the apertures 12 or depressions 14 or the average height of the discrete protruded elements 15 to the thickness of the precursor web 34 is at least about 1:1, at least about 2:1, at least about 3:1, at least about 4:1, at least about 5:1, or at least about 10:1. This ratio can be important to ensure the precursor web 34 and first embossed web 16A are sufficiently stretched so that each becomes permanently deformed to create the second embossed web 16B, especially at desirable process conditions and speed.

Forming structure 10 can be made of any material or materials that can be formed to have discrete forming elements 11 having the necessary dimensions to make an embossed web 16 and is dimensionally stable over process temperature and pressure ranges experienced by forming structure 10.

In one embodiment, discrete forming elements 11 are made integrally with forming structure 10. That is, the forming structure 10 is made as an integrated structure, either by removing material or by building up material. For example, the forming structure 10 having the required relatively small scale discrete forming elements 11 can be made by local, selective removal of material, such as by chemical etching, mechanical etching, or by ablating by use of high-energy sources such as electrical-discharge machines (EDM) or lasers, or by electron beam (e-beam), or by electrochemical machining (ECM). In one embodiment, the forming structure 10 may be constructed by a photo etched laminate process generally in accordance with the teachings of U.S. Pat. No. 4,342,314.

In one method of making a suitable forming structure 10, a base material susceptible to laser modification is laser "etched" to selectively remove material to form apertures 12 or depressions 14. By "susceptible to laser modification", it is meant that the material can be selectively removed by laser light in a controlled manner, recognizing that the wavelength of light used in the laser process, as well as the power level, may need to be matched to the material (or vice-versa) for optimum results. Laser etching can be achieved by known laser techniques, selecting wavelength, power, and time parameters as necessary to produce the desired protruded element dimensions. Currently known materials susceptible to laser modification include thermoplastics such as polypropylene, acetal resins such as DELRIN® from DuPont, Wilmington Del., USA, thermosets such as crosslinked polyesters, or epoxies, or even metals such as aluminum, copper, brass, nickel, stainless steel, or alloys thereof. Optionally, thermoplastic and thermoset materials can be filled with particulate or fiber fillers to increase compatibility with lasers of certain wavelengths of light and/or to improve modulus or toughness to make more durable apertures 12 or depressions 14. For example, certain polymers, such as PEEK, can be laser machined to higher resolution and at higher speeds by uniformly filling the polymer with sufficient amounts of hollow carbon nanotube fibers.

In one embodiment, a forming structure 10 can be laser machined in a continuous process. For example, a polymeric material such as DELRIN® can be provided in a cylindrical form as a base material having a central longitudinal axis, an outer surface, and an inner surface, the outer surface and inner surface defining a thickness of the base material. It can also be provided as a solid roll. A moveable laser source can be directed generally orthogonal to the outer surface. The moveable laser source can be moveable in a direction parallel to the central longitudinal axis of the base material. The cylindrical base material can be rotated about the central longitudinal axis while the laser source machines, or etches, the outer surface of the base material to remove selected portions of the base material in a pattern that defines a plurality of discrete apertures 12 or depressions 14 and/or discrete protruded elements 15.

The forming structure 10 can be in the form of a flat plate, a roll, a belt, an endless belt, a sleeve, or the like. In one preferred embodiment, the forming structure 10 is in the form of a roll. In another preferred embodiment, the forming structure 10 is in the form of an endless belt. Endless belts can be formed in accordance with the teachings of U.S. Pat. Nos. 7,655,176, 6,010,598, 5,334,289, and 4,529,480.

If the forming structure 10 includes protruded elements 15 and discrete apertures 12 and depressions 14, the discrete extended elements 22 can be formed in the embossed web 16 extending from the surface of the embossed web 16 opposite the surface from which the discrete extended elements 22 formed by the apertures 12 or depressions 14 of the forming structure 10 are formed. As a result, a two-sided embossed web 16 can be created, having different patterns or dimensions of extended elements 22 on each side of the embossed web 16. Depending upon the pressure generated between the forming structure 10 and compliant substrate 44, as well as the geometric shapes of the apertures 12 or depressions 14 and optional pillars or ridges of the forming structure 10, the discrete extended elements 22 of the embossed web 16 can have closed or open distal ends 24.

Pressure Source

The pressure source utilized to provide a force against the forming structure 10 can be, for example, a compliant substrate 44, a static pressure plenum 36, or combinations thereof. As used herein, "pressure source" refers to the first and/or second pressure sources as well as any additional pressure sources of additional embossing steps. The first and second pressure sources can be the same or different types of pressure sources. For example, the first and second pressure sources can both be static pressure plenums or compliant substrates. In another embodiment, the first pressure source can be a static pressure plenum 36 and the second pressure source can be a compliant substrate 44. In yet another embodiment, the first pressure source can be a compliant substrate 44 and the second pressure source can be static pressure plenum 36. In yet another embodiment, pressure from the same pressure source can be applied to both the first and second forming structures 10A, 10B in the first and second embossing steps.

Compliant Substrate

Figure 3:
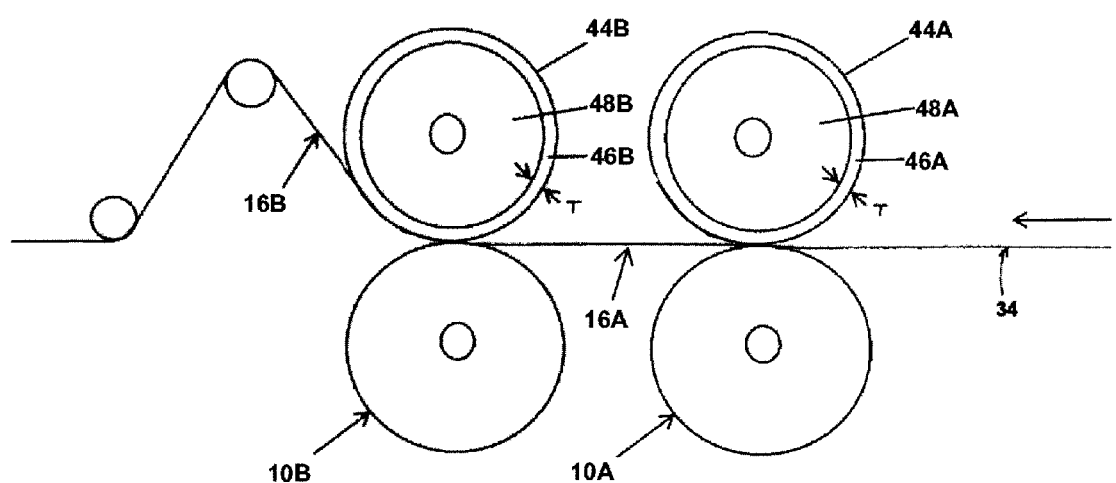
FIG. 3 is a schematic illustration of a continuous process for making an embossed web in accordance with an embodiment of the disclosure.

FIG. 3 illustrates a process in accordance with an embodiment of the disclosure in which the first and second pressure sources are each compliant substrates 44A, 44B. At a minimum, the outer surface of the compliant substrate 44A, 44B (i.e., the surface of the compliant substrate 44A, 44B oriented towards the forming structure 10A, 10B) includes a compliant material 46A, 46B. For example, the compliant substrate 44A, 44B can include a rigid material 48A, 48B covered by a compliant material 46A, 46B. The rigid material 48A, 48B can be a metal (such as steel), a plastic, or any other material that is significantly harder than the compliant material 46A, 46B. The thickness of the compliant material 46A, 46B covering the rigid material 48A, 48B will typically be no greater than about 26 mm, and preferably about 1 mm to about 26 mm, more preferably about 1 mm to about 7 mm. Alternatively, the entire compliant substrate 44 can be made of a compliant material 46A, 46B.

The compliant substrate 44A, 44B or compliant material 46A, 46B can include elastomers, felts, liquid-filled bladders, gas-filled bladders, and combinations thereof. In one embodiment, the compliant substrate 44A, 44B is a porous elastomer. The compliant substrate 44A, 44B, or the compliant material 46A, 46B utilized in the compliant substrate 44A, 44B, preferably has resilient properties (such as compression recovery) such that the compliant material 46A, 46B rebounds fast enough to facilitate the process, especially a continuous process.

The compliant substrate 44A, 44B, or the compliant material 46A, 46B utilized in the compliant substrate 44A, 44B, preferably also has enough durability to emboss large quantities of precursor web 34 material. As a result, the compliant substrate 44A, 44B preferably has a suitable degree of toughness and abrasion resistance, wherein the compliant substrate 44A, 44B will tend to be abraded by the forming structure 10 during the process.

The compliant substrate 44A, 44B can be in the form of a flat plate, a roll, a belt, an endless belt, a sleeve, or the like. In one embodiment, the compliant substrate 44A, 44B is a metal roll covered with a compliant material 46A, 46B, such as an elastomer. In another embodiment, the compliant substrate 44A, 44B and the forming structure 10A, 10B are both in the form of rolls. In another embodiment, the compliant substrate 44A, 44B is a roll that has a diameter greater than the diameter of the forming structure 10A, 10B roll. In another embodiment, the compliant substrate 44A, 44B is a roll that has a diameter less than the diameter of the forming structure 10A, 10B roll. In another embodiment, the compliant substrate 44A, 44B roll has a diameter that is the same as the diameter of the forming structure 10A, 10B roll. The first and second forming structures 10A, 10B can each be in the form of a roll having the same or different diameters. Alternatively, one forming structure 10, for example the first forming structure 10A, can be in the form of a plate, while the other forming structure 10B, for example, the second forming structure 10B can be in the form of a roll. Similarly, where the process includes the use of first and second compliant substrates 44A, 44B, each compliant substrate 44 can be in the form of a roll having the same or different diameters. Alternatively, one compliant substrates, for example the first compliant substrate 44A, can be in the form of a plate, while the other compliant substrate 44, for example, the second compliant substrate 10B can be in the form of a roll.

The compliant substrate 44A, 44B, or the compliant material 46A, 46B utilized in the compliant substrate 44A, 44B, will typically have a hardness of about 30 to about 90 durometer, preferably about 35 to about 80 durometer, and more preferably about 40 to about 70 durometer, on the Shore A scale. Hardness on the Shore A scale is typically determined by using an ASTM D2240 durometer, such as the Model 306 Type A Classic Style Durometer available from PTC Instruments of Los Angeles, Calif. It should be recognized that the compliant substrate 44A, 44B can exhibit varying hardness, for example lower hardness near the outer surface and higher hardness towards the inner surface of the compliant substrate 44A, 44B (i.e. varying hardness in the z-direction of the compliant substrate 44A, 44B) or varying hardness across the outer surface of the compliant substrate 44A. 44B (i.e. varying hardness in the x-y plane of the compliant substrate 44A, 44B). Where the process includes the use of first and second compliant substrates 44A, 44B, the compliant substrates can have the same or different hardness values.

The compliant material 46A, 46B utilized in the compliant substrate 44A, 44B will typically have a tensile modulus of about 1 to about 20 MPa, preferably about 2 to about 18 MPa, and more preferably about 3 to about 10 MPa. The tensile modulus of the compliant material 46A, 46B can be determined at a strain rate of 0.1 $\text{sec}^{-1}$.

Non-limiting examples of suitable compliant materials include natural rubber, urethane rubber, polyurethane rubber, chlorosulfonated polyethylene rubber (available under the tradename HYPALON® from DuPont), chloroprene rubber, norbornene rubber, nitrile rubber, hydrogenated nitrile rubber, styrene rubber, styrene-butadiene rubber, butadiene rubber, silicone rubber, ethylene-propylene-diene ("EPDM") rubber, isobutylene-isoprene rubber, felt (such as pressed wool felt), and the like. Particularly useful compliant materials are isoprene, EPDM, neoprene, and HYPALON® having a Shore A hardness of about 40 to about 70 durometer.

The compliant material 46A, 44B can also be a material that can be fed between a rigid material 48A, 48B and the forming structure 10A, 10B along with the precursor web 34 and first embossed web 16A. Such a material can serve to generate pressure against the precursor web 34 and first embossed web 16A and forming structure 10A, 10B so as to emboss the precursor web 34 and first embossed web 16A. Such a material can then be later incorporated, along with the embossed web 16, into a finished consumer product, such as a feminine hygiene product.

The compliant substrate 44A, 44B can optionally include recessed regions of a depth sufficient to prevent the embossing of the precursor web 34 and first embossed web 16A in the particular region, or only minimally emboss the precursor web 34 and first embossed web 16A in the particular region.

Static Pressure Plenum

Figure 4:
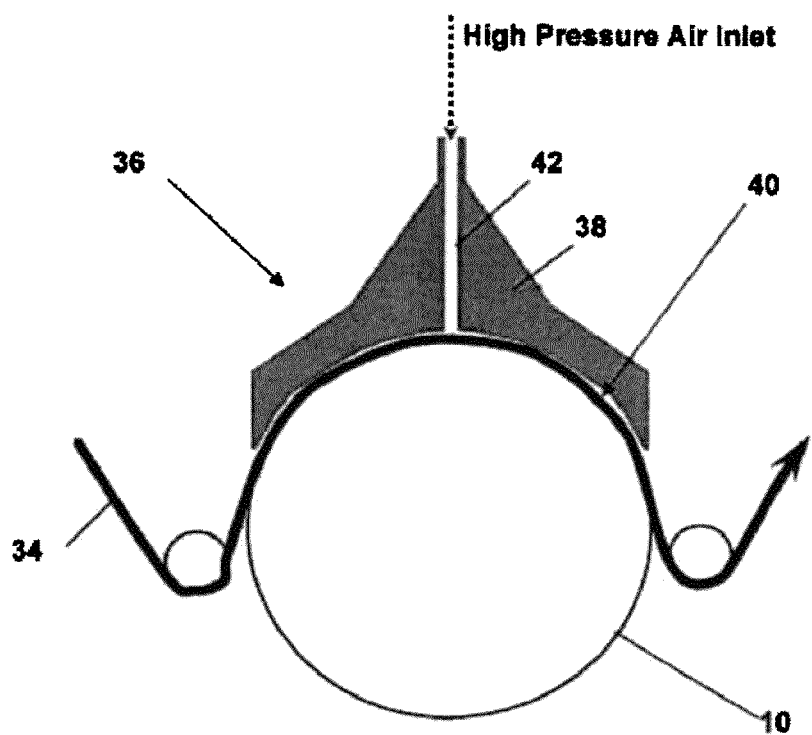
FIG. 4 is a schematic illustration of a process in accordance with an embodiment of the disclosure, illustrating a static gas pressure plenum.

Referring to FIG. 4, a static pressure plenum 36 is utilized to provide a force against the precursor web 34 and/or embossed web 16 to conform the precursor web 34 and/or embossed web 16 to the discrete forming elements 11 of the forming structure 10. Preferably, the static pressure plenum 36 is a static gas pressure plenum 36. The gas can be air, nitrogen, carbon dioxide, and combinations thereof. While only one static pressure plenum 36 is illustrated in FIG. 4, it is contemplated that one or both of the first and second pressure sources could be a static pressure plenum 36.

The static pressure plenum 36 exerts a pressure on the precursor web 34 and/or embossed web 16. The static gas pressure plenum 36 can include a hood 38 which defines a plenum 40 adjacent the precursor web 34 and/or embossed web 16. The hood 38 can include at least one high pressure gas inlet 42 allowing high pressure gas or other fluid to enter the hood 38 creating the static pressure conditions. Under static gas pressure conditions, there is no velocity and density impinging upon the precursor web 34 and/or embossed web 16 as with a velocity pressure source such as an air knife. Rather, a static high gas pressure is maintained in the hood 38 which creates a pressure differential across the webs, between the static pressure plenum 36 facing surface of the precursor web 34 and/or embossed web 16 and the forming structure 10 facing surface of the precursor web 34 and/or embossed web 16. The pressure differential is sufficient to conform the precursor web 34 and/or embossed web 16 to the discrete forming elements 11 of the forming structure 10. The pressure differential can be enhanced, for example, by applying a vacuum on the forming structure 10 facing surface of the precursor web 34 and/or embossed web 16.

Precursor Web

A precursor web 34 is converted into an embossed web 16 according to the process of the disclosure. Suitable precursor webs include materials that can be deformed by the pressure differential generated by the static pressure plenum 36 across the precursor web 34, such that the precursor web 34 is forced into conform to the discrete forming elements 11 of the forming structure 10 to produce an embossed web 16 having discrete extended elements 22. As used herein, "embossed web 16" refers to the first and/or second embossed webs 16A, 16B as well as any additional embossed webs formed by additional embossing steps.

The precursor web 34 typically includes synthetic material, metallic material, biological material (in particular, animal-derived materials), or combinations thereof. The precursor web 34 can optionally include cellulosic material. In one embodiment, the precursor web 34 is free of cellulosic material. Non-limiting examples of suitable precursor webs include films, such as polymeric or thermoplastic films, foils, such as metallic foils (e.g. aluminum, brass, copper, and the like), webs comprising sustainable polymers, foams, fibrous nonwoven webs comprising synthetic fibers (e.g. TYVEK®), collagen films, chitosan films, rayon, cellophane, and the like. Suitable precursor webs further include laminates or blends of these materials.

If the precursor web 34 is a fibrous nonwoven web, the fibrous web can have a high density such that it behaves similar to a film material. One example of such a high density fibrous web is TYVEK®. For nonwoven precursor webs 34, the precursor web 34 can comprise unbonded fibers, entangled fibers, tow fibers, or the like. Fibers can be extensible and/or elastic, and may be pre-stretched for processing. Fibers of precursor web 34 can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers.

Nonwoven precursor webs 34 can be any known nonwoven webs including nonwoven webs comprising polymer fibers having sufficient elongation properties to be formed into an embossed web 16. In general, the polymeric fibers can be bondable, either by chemical bond (e.g. by latex or adhesive bonding), pressure bonding, or thermal bonding. Nonwoven precursor web 34 can comprise about 100% by weight thermoplastic fibers. Nonwoven precursor web 34 can comprise as little as about 10% by weight thermoplastic fibers. Likewise, nonwoven precursor web 23 can comprise any amount by weight thermoplastic fibers in 1% increments between about 10% and about 100%.

The total basis weight of precursor web 34 (including laminate or multi-layer precursor webs 34) can range from about 8 gsm to about 500 gsm, depending on the ultimate use of the web 1, and can be produced in 1 gsm increments between about 8 and about 500 gsm, such as, for example, a precursor web 34 with a total basis weight from about 8 gsm to about 50 gsm. The constituent fibers of nonwoven precursor web 34 can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from about 0.1 to about 500 microns in 0.1 micron increments, such as, for example, from about 0.1 to about 50 microns.

The nonwoven precursor web 34 may be formed by known nonwoven extrusion processes, such as, for example, known meltblowing processes or known spunbonding processes.

The nonwoven precursor web 34 may be extensible, elastic, or nonelastic. The nonwoven precursor web 34 may be a spunbonded web, a meltblown web, or a bonded carded web. If the nonwoven precursor web 34 is a web of meltblown fibers, it may include meltblown microfibers. The nonwoven precursor web 34 may be made of fiber forming polymers such as, for example, polyolefins. Polyolefins include one or more of polypropylene, polyethylene, ethylene copolymers, propylene copolymers, and butene copolymers.

In one embodiment, the precursor web 34 is a polymeric film. Suitable polymeric films include thermoplastic films such as polyethylene, polypropylene, polystyrene, polyethylene terephthalate (PET), polymethylmethacrylate (PMMA), polyvinyl alcohol (PVA), nylon, polytetrafluoroethylene (PTFE) (e.g., TEFLON), or combinations thereof. Suitable polymeric films can include blends or mixtures of polymers.

In certain embodiments, the precursor web 34 can be a web comprising a sustainable polymer, such as polylactides, polyglycolides, polyhydroxyalkanoates, polysaccharides, polycaprolactones, and the like, or mixtures thereof.

The thickness of the precursor web 34 prior to embossing will typically range from about 5 to about 300 microns, about 5 microns to about 150 microns, about 5 microns to about 100 microns, or about 15 microns to about 50 microns. Other suitable thicknesses includes about 1, 2, 3, 4, 5, 6, 7, 8, 9, 10, 20, 30, 40, 50, 60, 70, 80, 90, 100, 150, 200, 250, or 300 microns.

Precursor webs, such as polymeric webs, will typically have a glass transition temperature of about −100° C. to about 120° C., or about −80° C. to about 100° C., or other suitable ranges. Precursor webs, such as polymeric webs, can have a melting point of about 100° C. to about 350° C. For example, a precursor web 34 formed of LDPE or a blend of LDPE and LLDPE has a melting pointing of about 110° C. to about 122°. A precursor web 34 formed of polypropylene has a melting point of about 165° C. A precursor web 34 formed of polyester has a melting point of about 255° C. A precursor web 34 formed of Nylon 6 has a melting point of about 215° C. A precursor web 34 formed of PTFE has a melting point of about 327° C.

In one embodiment, the process is carried out at a temperature less than the melting point of the precursor web 34. For example, the process can be carried out at 10° C. less than the melting point of the precursor web 34. In another embodiment, the process is carried out at a temperature substantially equal to the melting point of the precursor web 34. In one embodiment, the process is carried out at a temperature greater than the glass transition temperature of the precursor web 34.

Optionally, the precursor web 34 may be plasticized to make it less brittle prior to embossing in the process.

In one embodiment, the precursor web 34 is strain hardening. The strain hardening properties of the precursor web 34 can be desirable to facilitate conformation of the precursor web 34 to the discrete protruded elements 15 of the forming structure 10. This can be preferred for producing embossed webs wherein closed distal ends 24 of the extended elements 22 of the embossed web 16 are desired.

The precursor web 34 can be any material, such as a polymeric film, having sufficient material properties to be formed into an embossed web 16 described herein by the embossing process of the disclosure. The precursor web 34 will typically have a yield point and the precursor web 34 is preferably stretched beyond its yield point to form an embossed web 16. That is, the precursor web 34 should have sufficient yield properties such that the precursor web 34 can be strained without rupture to an extent to produce the desired discrete extended elements 22 with closed distal ends 24 or, in the case of an embossed web 16 comprising discrete extended elements 22 having open distal ends 24, rupture to form open distal ends 24. As disclosed below, process conditions such as temperature can be varied for a given polymer to permit it to stretch with or without rupture to form the embossed web 16 having the desired discrete extended elements 22. In general, therefore, it has been found that preferred starting materials to be used as the precursor web 34 for producing the embossed web 16 exhibit low yield and high-elongation characteristics. In addition, as discussed previously, the precursor webs preferably strain harden. Examples of films suitable for use as the precursor web 34 include films comprising low density polyethylene (LDPE), linear low-density polyethylene (LLDPE), and blends of linear low-density polyethylene and low density polyethylene (LLDPE/LDPE).

Precursor web 34 should also be sufficiently deformable and have sufficient ductility for use as a precursor web 34. The term "deformable" as used herein describes a material which, when stretched beyond its elastic limit, will substantially retain its newly formed conformation, as well as exhibit thinning at the distal ends 24 and/or along the sidewalls of the discrete extended elements 22 of the resulting embossed web 16.

One material found suitable for use as a precursor web 34 is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882). Other suitable precursor webs include polyethylene film that is about 25 microns (1.0 mil) thick and has a basis weight of about 24 grams per square meter ("gsm") available from available from RKW US, Inc. (Rome, Ga.) and polyethylene/polypropylene film having a basis weight of about 14 gsm and a thickness of about 15 microns available from RKW US, Inc.

The precursor web 34 can be a laminate of two or more webs, and can be a co-extruded laminate. For example, precursor web 34 can include two layers, and precursor web 34 can include three layers, wherein the innermost layer is referred to as a core layer, and the two outermost layers are referred to as skin layers. In one embodiment, the precursor web 34 includes a three layer coextruded laminate having an overall thickness of about 25 microns (0.001 in.), with the core layer having a thickness of about 18 microns (0.0007 in.); and each skin layer having a thickness of about 3.5 microns (0.00015 in.). In one embodiment, the layers can include polymers having different stress-strain and/or elastic properties.

The precursor web 34 can be made using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a pre-compounding extruder followed by repelletization prior to film extrusion. Suitable methods for making precursor web 34 are disclosed in U.S. Pat. No. 5,520,875 and U.S. Pat. No. 6,228,462.

In general, the ability to form high area density (or low average center-to-center spacing) discrete extended elements 22 on the embossed web 16 can be limited by the thickness of precursor web 34 due to edge to edge spacing limitations; however, in certain embodiments, processes set forth herein can overcome this limitation by using wider edge-to-edge spaced forming elements.

In certain embodiments, the precursor web 34 can optionally further include a surfactant. If utilized, preferred surfactants include those from non-ionic families such as: alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, ethoxylated anhydrosorbitol esters, ethoxylated natural fats, oils, and waxes, glycol esters of fatty acids, carboxylic amides, diethanolamine condensates, and polyalkyleneoxide block copolymers. Molecular weights of surfactants selected can range from about 200 grams per mole to about 10,000 grams per mole. Preferred surfactants have a molecular weight of about 300 to about 1,000 grams per mole.

If utilized, the surfactant level initially blended into precursor web 34 can be as much as 10 percent by weight of the total precursor web 34. Surfactants in the preferred molecular weight range (300-1,000 grams/mole) can be added at lower levels, generally at or below about 5 weight percent of the total precursor web 34.

In certain embodiments, the precursor web 34 can also include titanium dioxide in the polymer blend. Titanium dioxide can provide for greater opacity of the embossed web 16. Titanium dioxide can be added at up to about 10 percent by weight of the precursor web 34, such as low density polyethylene.

Other additives, such as particulate material, e.g., carbon black, iron oxide, mica, calcium carbonate ($CaCO_3$), particulate skin treatments or protectants, or odor-absorbing actives, e.g., zeolites, can optionally be added in one or more layers of precursor web 34. In some embodiments, embossed webs comprising particulate matter, when used in skin-contacting applications, can permit actives to contact the skin in a very direct and efficient manner. Specifically, in some embodiments, formation of discrete extended elements 22 can expose particulate matter at or near the distal ends 24 thereof. Therefore, actives such as skin care agents can be localized at or near distal ends 24 of the discrete extended elements 22 to permit direct skin contact with such skin care agents when the embossed web 16 is used in skin contacting applications.

The average particle size of the particulate material, if utilized in the precursor web 34, will typically be 0.2 to about 200 microns or about 5 microns to about 100 microns. The use of certain particulate materials, such as mica interference particles, can dramatically improve the visual appearance of the embossed web 16.

The precursor web 34 can also optionally include colorants, such as pigment, lake, toner, dye, ink or other agent used to impart a color to a material, to improve the visual appearance of the embossed web 16.

Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like.

Suitable colored webs are described in co-pending U.S. application Ser. No. 12/721,947, filed Mar. 11, 2010 entitled "COLORED WEB MATERIAL COMPRISING A PLURALITY OF DISCRETE EXTENDED ELEMENTS" and U.S. application Ser. No. 12/721,965, filed Mar. 11, 2010 entitled "WEB MATERIAL EXHIBITING VIEWING-ANGLE DEPENDENT COLOR AND COMPRISING A PLURALITY OF DISCRETE EXTENDED ELEMENTS".

The precursor web 34 can also optionally include fillers, plasticizers, and the like.

Embossed Web

Figure 5:
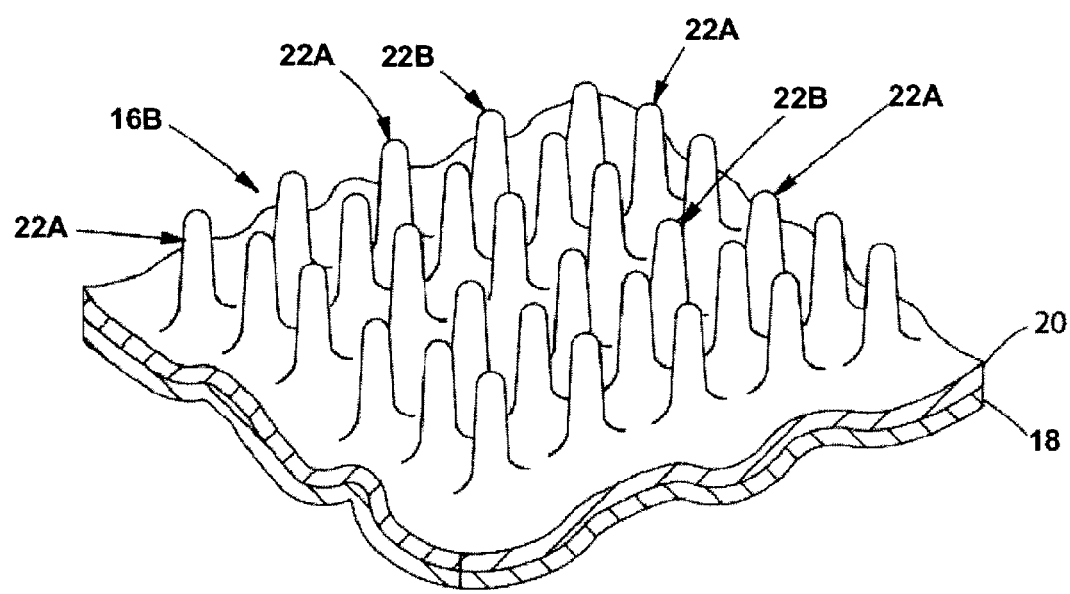
FIG. 5 is a perspective view of a portion of an embossed web formed by a process in accordance with an embodiment of the disclosure.
Figure 6:
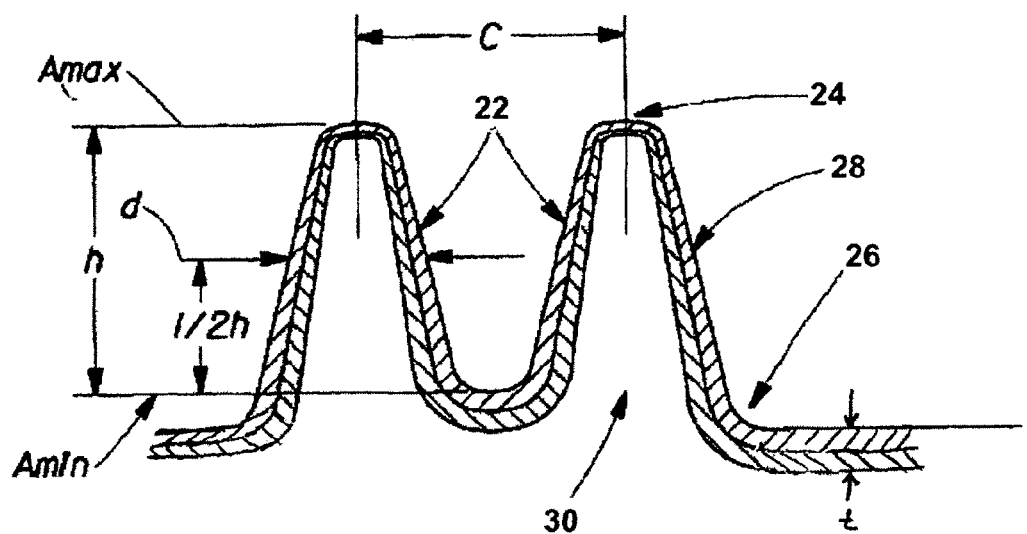
FIG. 6 is a cross-sectional view of a portion of an embossed web formed by a process in accordance with an embodiment of the disclosure.
Figure 7:
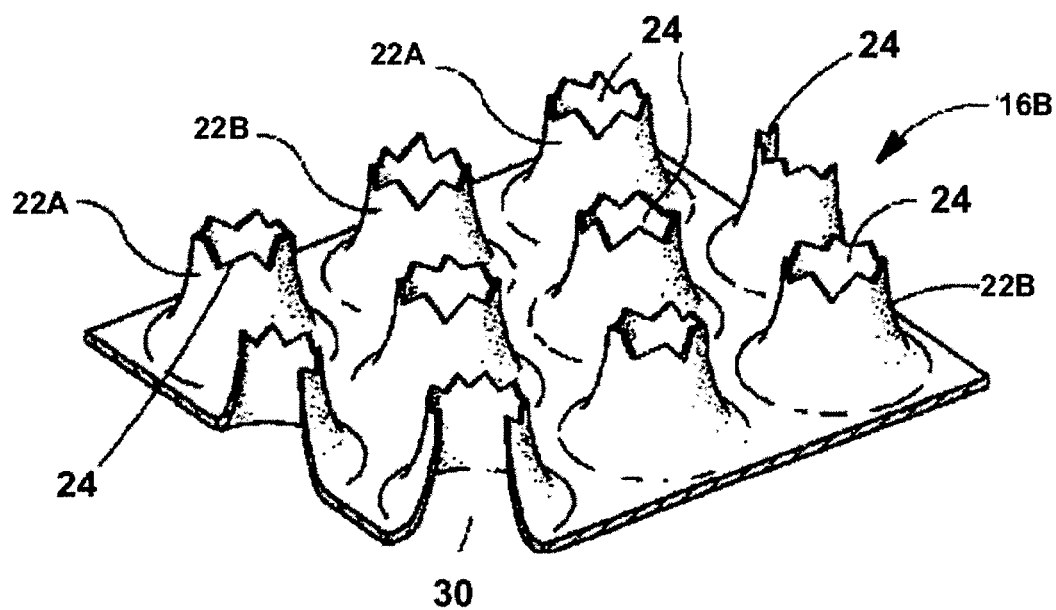
FIG. 7 is a perspective view of a portion of an embossed web having discrete extended elements with open distal ends formed by a process in accordance with an embodiment of the disclosure.

The precursor web 34 is processed according to the process of the disclosure to form an embossed web 16 that can have various desired structural features and properties such as desired soft hand feel and an aesthetically pleasing visual appearance. The precursor web 34 is positioned between the first forming structure 10A and the first pressure source provided to conform the precursor web 34 to the discrete first forming elements 11A of the first forming structure 10A. A first embossed web 16A having first discrete extended elements 22A is thereby produced. The first embossed web 16A is then positioned between the second forming structure 10B and the second pressure source provided to conform the precursor web 34 to the discrete second forming elements 10B of the second forming structure. Referring to FIG. 5, a second embossed web 16B having second discrete extended elements 22B in addition to the first discrete extended elements 22A is thereby produced. As shown in FIG. 5, the second discrete extended elements 22A can be formed adjacent to the first discrete extended elements 22A. In another embodiment, the embossed web 16 can include second discrete extended elements 22A formed at least partially overlapping with the first discrete extended elements 22A. In yet another embodiment, the placement of the precursor and first embossed web 16A on the first and second forming structures 10A, 10B, respectively, and/or the spacing and density of the forming elements 11 on the first and second forming structures 10A, 10B can be used to control the position of the second discrete extended elements 22A relative to the first extended elements 22A. For example, the position of the first embossed web 16A along with the spacing and density of the second forming elements 11B as compared to the spacing and density of the first forming elements 11A can be controlled so as to space the second discrete extended elements 22A halfway between adjacent first discrete extended elements 22A, thereby producing an embossed web 16 having equidistant discrete extended elements 22. As shown in FIG. 6, the discrete extended elements 22 have open proximal ends 30 and open (as shown in FIG. 6) or closed distal ends 24 (as shown in FIG. 7). For example, the first discrete extended elements 22A can have open distal ends 24, while the second discrete extended elements 22B have closed distal ends 24. In another embodiment the first discrete extended elements 22A can have closed distal ends 24, while the second discrete extended elements 22B have open distal ends 24. Alternatively, the first and second discrete extended elements 22A, 22B can have the same type of distal ends 24, either open or closed.

In one embodiment, the embossed web 16 resulting from the process described herein can have a structure similar to that described in detail in U.S. Pat. Nos. 7,402,723 or 7,521,588. Advantageously, the process disclosed herein can allow for use of forming structures 10 having wider edge-to-edge spacing between adjacent forming elements 11 as well as a lower density of forming elements 11, while producing embossed webs having smaller scale spacing between adjacent discrete extended elements 22 and a high density of discrete extended elements 22 such as would be produced by a single forming structure 10 having a small edge-to-edge spacing between adjacent forming elements 11 and a high density of forming elements 11. Such forming structures 10 having few forming elements 11 and wider spacing between adjacent elements 11 are cheaper and easier to manufacture and have significantly increased life span as compared to forming structures 10 having a higher area density of forming elements 11 with narrower spacing between adjacent elements 11. In addition, when a compliant substrate is used, a sizable increase in substrate lifetime can be observed when using such a forming structure. While not being bound by theory, it is believed that the increase in lifetime is due to the reduction in tensile stresses on the compliant substrate as it is being forced down between adjacent protruded elements. For example, a $10^4$ times increase in lifespan of the compliant substrate can be achieved by increasing the edge-to-edge spacing between adjacent forming elements 11 from about 250 μm to about 400 μm. When a gas pressure plenum is used, lower pressures can be used as the edge-to-edge distance is increased.

The three-dimensional embossed web 16 is produced from a precursor web 34, which can be a single layer of web material or a multilayer coextruded or laminate web material as described hereinbefore. Laminate film materials may be coextruded, as is known in the art for making laminate films, including films comprising skin layers. In the embodiment illustrate in FIG. 5, the precursor web 34 is a two layer laminate film comprising a first layer 18 and a second layer 20.

The discrete extended elements 22 are formed as protruded extensions of the web, generally on a first surface 26 thereof. The number, size, and distribution of discrete extended elements 22 on the embossed web 16 can be predetermined based on desired soft feel and visual effects. For applications such as a topsheet, backsheet or release paper wrapper in disposable absorbent articles, or packaging, it can be desired that the discrete extended elements 22 protrude only from one surface of embossed web 16. Therefore, when the embossed web 16 is used as a topsheet in a disposable absorbent article, the embossed web 16 can be oriented such that the discrete extended elements 22 are skin contacting for superior softness impression. Moreover, having discrete extended elements 22 with closed distal ends 24 can result in reduced rewet, i.e., reduced amounts of fluid being re-introduced to the surface of the topsheet after having been first passed through apertures of the topsheet to underlying absorbent layers.

Referring to FIG. 6, the discrete extended elements 22 can be described as protruding from a first surface 28 of the embossed web 16. As such, the discrete extended elements 22 can be described as being integral with precursor web 34, and formed by permanent local plastic deformation of the precursor web 34. The discrete extended elements 22 can be described as having a side wall(s) 28 defining an open proximal portion 30 and a closed or open distal end 24. The discrete extended elements 22 each have a height h measured from a minimum amplitude $A_{min}$ between adjacent extended elements 22 to a maximum amplitude $A_{max}$ at the closed or open distal end 24. The discrete extended elements 22 have a diameter d, which for a generally cylindrical structure 10 is the outside diameter at a lateral cross-section. By "lateral" is meant generally parallel to the plane of the first surface 26. For generally columnar discrete extended elements 22 having non-uniform lateral cross-sections, and/or non-cylindrical structures of discrete extended elements 22, diameter d is measured as the average lateral cross-sectional dimension at ½ the height h of the discrete extended element. Thus, for each discrete extended element, an aspect ratio, defined as h/d, can be determined The discrete extended element can have an aspect ratio h/d of at least about 0.2, at least about 0.3, at least about 0.5, at least about 0.75, at least about 1, at least about 1.5, at least about 2, at least about 2.5, or at least about 3. The discrete extended elements 22 will typically have a height h of at least about 30 microns, at least about 50 microns, at least about 65, at least about 80 microns, at least about 100 microns, at least about 120 microns, at least about 150 microns, or at least about 200 microns. The extended elements 22 will typically be at least the same height as the thickness of the precursor web 34, or at least 2 times the thickness of the precursor web 34, or preferably at least 3 times the thickness of the precursor web 34. The discrete extended elements 22 will typically have a diameter d of about 50 microns to about 5,000 microns, about 50 microns to about 3,000 microns, about 50 microns to about 500 microns, about 65 microns to about 300 microns, or about 75 microns to about 200 microns. In certain embodiments, the discrete extended elements 22 can have larger diameters d up to about 2.5 centimeters, up to about 2 centimeters, up to about 1.5 centimeters, up to about 1 cm, up to about 0.5 centimeters, or up to about 0.1 centimeters.

For discrete extended elements 22 that have generally non-columnar or irregular shapes, a diameter of the discrete extended element can be defined as two times the radius of gyration of the discrete extended element at ½ height.

For discrete extended elements 22 that have shapes, such as ridges, that extend lengthwise across the entire web material such that the extended elements 22 have a portion of the sidewalls of the extended elements 22 that are open, a diameter of a discrete extended element can be defined as the average minimal width between two opposing sidewalls of the extended element at ½ height.

In general, because the actual height h of any individual discrete extended element can be difficult to determine, and because the actual height may vary, an average height $h_{avg}$ of a plurality of discrete extended elements 22 can be determined by determining an average minimum amplitude $A_{min}$ and an average maximum amplitude $A_{max}$ over a predetermined area of the embossed web 16. Such average height $hp_{avg}$ will typically fall within the ranges of heights described above. Likewise, for varying cross-sectional dimensions, an average diameter $d_{avg}$ can be determined for a plurality of discrete extended elements 22. Such average diameter $d_{avg}$ will typically fall within the ranges of diameters described above. Such amplitude and other dimensional measurements can be made by any method known in the art, such as by computer aided scanning microscopy and data processing. Therefore, an average aspect ratio $AR_{avg}$ of the discrete extended elements 22 for a predetermined portion of the embossed web 16 can be expressed as $h_{avg}/d_{avg}$.

In one embodiment, the diameter of a discrete extended element is constant or decreases with increasing amplitude (amplitude increases to a maximum at closed or open distal end 24). The diameter, or average lateral cross-sectional dimension, of the discrete extended elements 22 can be a maximum at proximal portion and the lateral cross-sectional dimension steadily decreases to distal end. This structure 10 is believed to be desirable to help ensure the embossed web 16 can be readily removed from the forming structure 10. In another embodiment, the diameter of the discrete extended elements 22 increases with increasing amplitude. For example, the discrete extended elements 22 can have a mushroom shape.

Thinning of the precursor web 34 can occur due to the relatively deep drawing required to form high aspect ratio discrete extended elements 22. For example, thinning can be observed at the closed or open distal ends 24 and/or along the sidewalls. By "observed" is meant that the thinning is distinct when viewed in magnified cross-section. Such thinning can be beneficial as the thinned portions offer little resistance to compression or shear when touched. For example, when a person touches the embossed web 16 on the side exhibiting discrete extended elements 22, the fingertips of the person first contact the closed or open distal ends 24 of the discrete extended elements 22. Due to the high aspect ratio of the discrete extended elements 22, and the wall thinning of the precursor web 34 at the distal ends 24 and/or along the sidewalls, the discrete extended elements 22 offer little resistance to the compression or shear imposed on the embossed web 16 by the person's fingers. This lack of resistance is registered as a feeling of softness, much like the feeling of a velour fabric.

Thinning of the precursor web 34 at the closed or open distal ends 24 and/or along the sidewalls can be measured relative to the thickness of the precursor web 34 or relative to the thickness of the land area that completely surrounds the discrete extended elements 22 of the embossed web 16. The precursor web 34 will typically exhibit thinning of at least about 25%, at least about 50%, or at least about 75% relative to the thickness of the precursor web 34. The precursor web 34 will typically exhibit thinning of at least about 25%, at least about 50%, or at least about 75%, at least about 85% relative to the thickness of the land area surrounding the discrete extended elements 22 of the embossed web 16.

It should be noted that a fluid impermeable web having only the discrete extended elements 22 as disclosed herein, and not having macroscopic apertures 12 or discrete extended elements 22 having open distal ends 24, can offer softness for any application in which fluid permeability is not required. Thus, in one embodiment, the process produces an embossed web 16 exhibiting a soft and silky tactile impression on at least one surface thereof, the silky feeling surface of the embossed web 16 exhibiting a pattern of discrete extended elements 22, each of the discrete extended elements 22 being a protruded extension of the web surface and having a side wall defining an open proximal portion 30 and a closed distal end 24, the discrete extended elements 22 having a maximum lateral cross-sectional dimension at or near the open proximal portion 30.

The embossed web 16 can also exhibit improved sound effects. For example, when handled or manually manipulated, the embossed web 16 creates less sound as compared to the precursor web 34.

The "area density" of the discrete extended elements 22, which is the number of discrete extended elements 22 per unit area of first surface 26, can be optimized and the embossed web 16 will typically include about 0.1 to about 10,000, 4 to about 10,000, about 95 to about 10,000, about 240 to about 10,000, about 350 to about 10,000, about 500 to about 5,000, or about 700 to about 3,000 discrete extended elements 22 per square centimeter. In general, the center-to-center spacing can be optimized for adequate tactile impression, while at the same time minimizing entrapment of materials, such as fluids, between discrete extended elements 22. The center-to-center spacing between adjacent discrete extended elements 22 can be about 100 microns to about 1,000 microns, about 30 microns to about 800 microns, about 150 microns to about 600 microns, or about 180 microns to about 500 microns.

When the embossed web 16 is utilized as a topsheet for disposable absorbent articles, the embossed web 16 can further include macroapertures that allow fluid to flow through the embossed web 16.

Process for Making Embossed Web

Referring again to FIG. 3, the first embossing process for forming a first embossed web 16A includes feeding the precursor web 34 between the first pressure source and the first forming structure 10A and applying a pressure from the first pressure source against the precursor web 34 and the first forming structure 10A sufficient to force portions of the precursor web 34 to conform to the discrete first forming elements 11A of the first forming structure 10A to thereby form a first embossed web 16A having first discrete extended elements 22A. The conformation of the precursor web 34 to the first forming structure 10A can be partial conformation, substantial conformation, or complete conformation, depending upon the pressure generated and the topography of the first forming structure 10A. The second embossing process includes feeding the first embossed web 16A between the second pressure source and the second forming structure 10B and applying a pressure from the second pressure source against the first embossed web 16A and the second forming structure 10B sufficient to force portions of the first embossed web 16A to conform to the discrete second forming elements 11B of the second forming structure 10B to thereby form a second embossed web 16B having second discrete extended elements 22B as well as the first discrete extended elements 22A. The conformation of the first embossed web 16A to the second forming structure 10B can be a partial conformation, substantial conformation, or complete conformation, depending upon the pressure generated and the topography of the second forming structure.

While not being bound by theory, it is believed that when the forming structure 10 includes apertures 12 or depressions open distal ends 24 can be formed by locally rupturing the precursor web 34 while forcing the precursor web 34 into the apertures 12 or depressions 14 of the forming structure 10. When the forming structure 10 includes discrete protruded elements 15, factors such as the shape of the protrusion and the pressure applied can be adjusted to produce discrete extended elements 22 with either closed or open distal ends 24.

To obtain permanent deformation of the precursor web 34 and the first embossed web 16A to form the first embossed web 16A and the second embossed web 16B, respectively, the applied pressure is generally sufficient to stretch the precursor beyond its yield point.

The process can be a batch process or a continuous process. A batch process can involve providing individual sheets of precursor web 34 material placed between the first forming structure 10A and the first pressure source to form sheets of a first embossed web 16A, and then providing individual sheets of the first embossed web 16A between the second forming structure 10B and the second pressure source to form sheets of a second embossed web 16B.

As illustrated in FIG. 3, a continuous process can involve providing a roll of precursor web 34 material that is unwound and fed between the first forming structure 10A and first pressure source to form a first embossed web 16A. The process then includes feeding the first embossed web 16A between the second forming structure 10B and the second pressure source to form the second embossed web 16B. The first and/or second forming structure 10A, 10B can be, for example, in the form of a roll. As the precursor web 34 and the first embossed web 16A pass between the first and second forming structure 10A, 10B rolls and the first and second pressure sources, first and second embossed webs 16A, 16B are formed, respectively.

The process can have relatively short dwell times. As used herein, the term "dwell time" refers to the amount of time pressure is applied to a given portion of the precursor web 34 or the first embossed web 16A, usually the amount of time a given portion of the precursor web 34 or the first embossed web 16A spends positioned between the first and second forming structures 10A, 10B and the first and second pressure sources. The pressure is typically applied to the precursor web 34 or the first embossed web 16A for a dwell time of less than about 5 seconds, less than about 1 second, less than about 0.5 second, less than about 0.1 second, less than about 0.01 second, or less than about 0.005 second. For example, the dwell time can be about 0.5 milliseconds to about 50 milliseconds. The pressure can be applied to the precursor web 34 by the first pressure source for a first dwell time and pressure can be applied to the first embossed web 16A by the second pressure source for a second dwell time. The first and second dwell times can be substantially equal or can be different. Even with such relatively short dwell times, embossed webs can be produced with desirable structural features described herein. As a result, the process of the disclosure enables high speed production of embossed webs.

The precursor web 34 or the first embossed web 16A can be fed between the first and second forming structures 10A, 10B and the first and second pressure source at a rate of at least about 0.01 meters per second, at least about 1 meter per second, at least about 5 meters per second, or at least about 10 meters per second. Other suitable rates include, for example, at least about 0.01, 0.05, 0.1, 0.5, 1, 2, 3, 4, 5, 6, 7, 8, 9, or 10 meters per second. The rate at which the precursor web 34 is fed between the first forming structure 10A and the first pressure source can be substantially the same or different as the rate the first embossed web 16A is fed between the second forming structure 10B and the second pressure source.

Depending upon factors such as the shape of the discrete forming elements 11 on the forming structure 10 and the pressure applied, the distal ends 24 of the extended elements 22 of the embossed web 16 produced by the process of the disclosure can be either closed or open.

Any or each of the embossing steps of the process can be carried out at ambient temperature, meaning that no heat is intentionally applied to the forming structure 10 and/or precursor web 34. It should be recognized, however, that heat can be generated due to the pressure between the forming structure 10 and the pressure source, especially in a continuous process. As a result, the forming structure 10 and/or the pressure source may be cooled in order to maintain the process conditions at the desired temperature, such as ambient temperature. For example, a cooled compliant substrate 44 or a cooled fluid pressure source for the static pressure plenum 36 can be used.

Any or each of the embossing steps of the process can also be carried out with the web having an elevated temperature. For example, the temperature of the web can be less than the melting point of the precursor web 34. For example, the temperature of the web can be at least about 10° C. below the melting point of the precursor web 34. The web, especially a web including polyethylenes, can have a temperature during the process of about 10° C. to about 200° C., about 10° C. to about 120° C., about 20° C. to about 110° C., about 10° C. to about 80° C., or about 10° C. to about 40° C. The web can be heated during the process by heating the web, using a heated compliant substrate 44 or a heated fluid pressure source for the static pressure plenum 36, and/or by heating the forming structure 10. For example, a heated gas can be used as the pressure source for the static pressure plenum 36.

In one embodiment, the web is not heated before being provided between the forming structure 10 and the pressure source. In another embodiment, the web, the forming structure 10 and the pressure source are not heated before providing the web between the forming structure 10 and the pressure source.

In general, the process can be carried out at a temperature of from about 10° C. to about 200° C., from about 10° C. to about 120° C., from about 10° C. to about 80° C., or from about 10° C. to about 40° C. The temperature can be measured by, for example, a non-contact thermometer, such as an infrared thermometer or a laser thermometer, measuring the temperature at the nip between the compliant substrate 44 and forming structure 10. The temperature can also be determined using temperature sensitive material such as Thermolabel available from Paper Thermometer Company.

An average pressure is provided by the static pressure plenum 36. The average pressure is sufficient to force the precursor web 34, which is positioned between the forming structure 10 and static pressure plenum 36, into the discrete apertures 12 or depressions 14 of the forming structure 10 to form an embossed web 16. In general, the average pressure provided between the forming structure 10 and static pressure plenum 36 is about 0.1 MPa to about 25 MPa, about 1 MPa to about 20 MPa, about 0.5 MPa to about 10 MPa, about 10 MPa to about 25 MPa, or about 0.5 MPa to about 5 MPa.

An average pressure is provided between the compliant substrate 44 and the forming structure 10. The average pressure is sufficient to force the precursor web 34, which is positioned between the forming structure 10 and compliant substrate 44, into the discrete apertures 12 or depressions 14 of the forming structure 10 to form an embossed web 16. In general, the average pressure provided between the forming structure 10 and compliant substrate 44 is about 1 MPa to about 100 MPa, about 5 MPa to about 70 MPa, about 10 MPa to about 60 MPa, or about 20 MPa to about 40 MPa. For example, the applied pressure can be up to about 30 MPa.

The average pressure provided between the forming structure 10 and the compliant substrate 44 can be determined as a force per unit area. A force is applied to the forming structure 10 and/or compliant substrate 44 so that the compliant substrate 44 becomes impressed against the forming structure 10 to a desired compression distance, as described herein below. The unit area is the area of the "contact patch" between the forming structure 10 and the compliant substrate 44. From these values, an average pressure between the forming structure 10 and compliant substrate 44 can be calculated.

If the forming structure 10 and compliant substrate 44 are both flat plates, the area of the contact patch between the forming structure 10 and compliant substrate 44 is typically easily determined based on the dimensions of the flat plates.

If the forming structure 10 and the compliant substrate 44 are both rolls, the area of the contact patch between the forming structure 10 and compliant substrate 44 can be determined by static loading of the rolls with a piece of pressure sensitive film provided between the rolls. A suitable pressure sensitive film is Fuji Prescale Film available from FUJIFILM NDT Systems, which undergoes certain color changes upon application of pressure to the film. The static loading on the rolls is released and the pressure sensitive film is removed from the rolls. The pressure sensitive film will have a color-changed area that represents the contact patch between the forming structure 10 and compliant substrate 44. Using this contact patch area and the force applied to the forming structure 10 roll and/or compliant structure 10 roll, the average pressure provided between the forming structure 10 roll and compliant structure 10 roll can be calculated.

The forming structure 10 and compliant substrate 44 are impressed to a desired compression distance by applying a force to the forming structure 10 and/or compliant substrate 44. The "compression distance" is determined by measuring the distance the forming structure 10 is pressed against the compliant substrate 44. This distance can be measured by bringing the forming structure 10 and compliant substrate 44 into initial contact and then forcing the forming structure 10 and compliant substrate 44 together. The distance that the forming structure 10 and compliant substrate 44 are moved relative to each other subsequent to the initial contact is referred to as the "compression distance". If the forming structure 10 and compliant substrate 44 are both rolls, the compression distance can be measured as the change in distance between the rotational axis of the forming structure 10 and the rotational axis of the compliant substrate 44 due to the force applied after initial contact.

The compression distance of the forming structure 10 to the compliant substrate 44 will typically be about 1 mm to 10 mm, about 0.1 mm to about 5 mm, about 0.2 mm to about 4 mm, or about 0.3 mm to about 3 mm.

The process can optionally further include applying a slip agent to the precursor web 34 and/or the forming structure 10 and/or the pressure source (if a compliant substrate 44 is used) before the precursor web 34 is provided between the forming structure 10 and the pressure source. This can be beneficial, especially in a continuous process, to reduce friction between the precursor web 34 and the forming structure 10. Non-limiting examples of suitable slip agents include silicone, talc, lubricating oils, and the like.

The process can optionally include applying a positive pressure to the embossed web 16 to reinvert discrete extended elements 22 that may have inverted during removal of the embossed web 16 from between the forming structure 10 and the pressure source. The inverted discrete extended elements 22 can be reinverted to extend from the embossed web first surface 26 by applying a positive pressure, such as from an air knife, sufficient to reinvert the inverted discrete extended elements 22.

The process can optionally be combined with other processes to further manipulate the embossed web 16. In one embodiment, such additional processes can be combined with the process on the same process manufacturing line to produce, for example, absorbent articles. In one embodiment, the process is combined with a process that can impart macroapertures in the embossed web 16, such as the process described in US 2006/0087053 A1 or US 2005/0064136 A1. Such a process combination can produce a macroapertured embossed web 16 that can be suitable for use as a topsheet in an absorbent article. Such a macroapertured embossed web 16 can be subsequently converted into an absorbent article by combining it with other absorbent article components, such as absorbent cores, backsheets, and the like, preferably on the same process manufacturing line.

Uses of Embossed Web

The embossed webs can be utilized in a number of different ways, including as component materials of absorbent articles (such as topsheets, backsheets or release paper wrappers), packaging (such as flow wrap, shrink wrap, or polybags), trash bags, food wrap, dental floss, wipes, electronic components, wall paper, clothing, aprons, window coverings, placemats, book covers, and the like.

EXAMPLES

Example 1

Embossing Process Using the Same Forming Structure and Pressure Source

Embossed webs were produced using the same forming structure 10 as the first and second forming structures 10A, 10B and using a compliant substrate 44 as the first and second pressure sources. The forming structures 10A, 10B included about 600 protruded elements 15 per square centimeter (a 60 mesh cylindrical forming structure 10). The forming structures 10A, 10B were made from a Delrin roll with a diameter of about 205 mm. The protruded elements 15 have a circular cross-section with a diameter of about 150 microns and a center-to-center spacing of about 423 microns. The protruded elements 15 have straight sidewalls with a slight inward taper and the tips are rounded.

The compliant substrate 44 used as the first and second pressure sources was formed of rubber coated steel roll and obtained from American Roller Company (1440 13$^{th}$ Ave, Union Grove, Wisc., USA, 53182). There are two layers of rubber. The base layer is 6 mm thick, made from nitrile rubber and has a Shore A hardness of about 95. The outer layer is 2 mm thick nitrile rubber and has a Shore A hardness of about 65.

The precursor web 34 utilized is a polyethylene film, obtained from the RKW-Group, Germany, that is about 25 microns thick and has a basis weight of about 24 grams per square meter (gsm). It has a fine square embossed pattern on it.

The embossing process is performed by feeding the precursor web into the nip of compliant substrate 44 and forming structure 10 with roll diameters of 205 mm at a rate of about 1 m/sec.

Figure 8A:
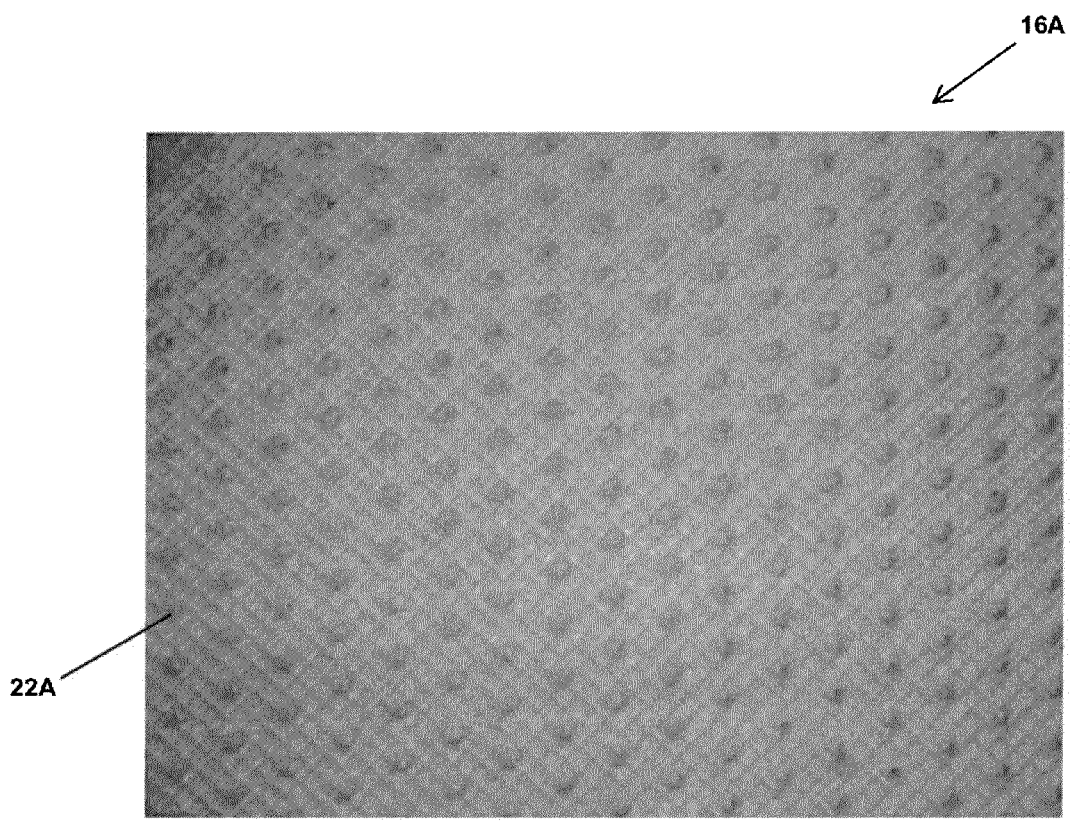
FIG. 8A is a photograph of a first embossed web having first discrete extended elements formed by a process in accordance with an embodiment of the disclosure.
Figure 8B:
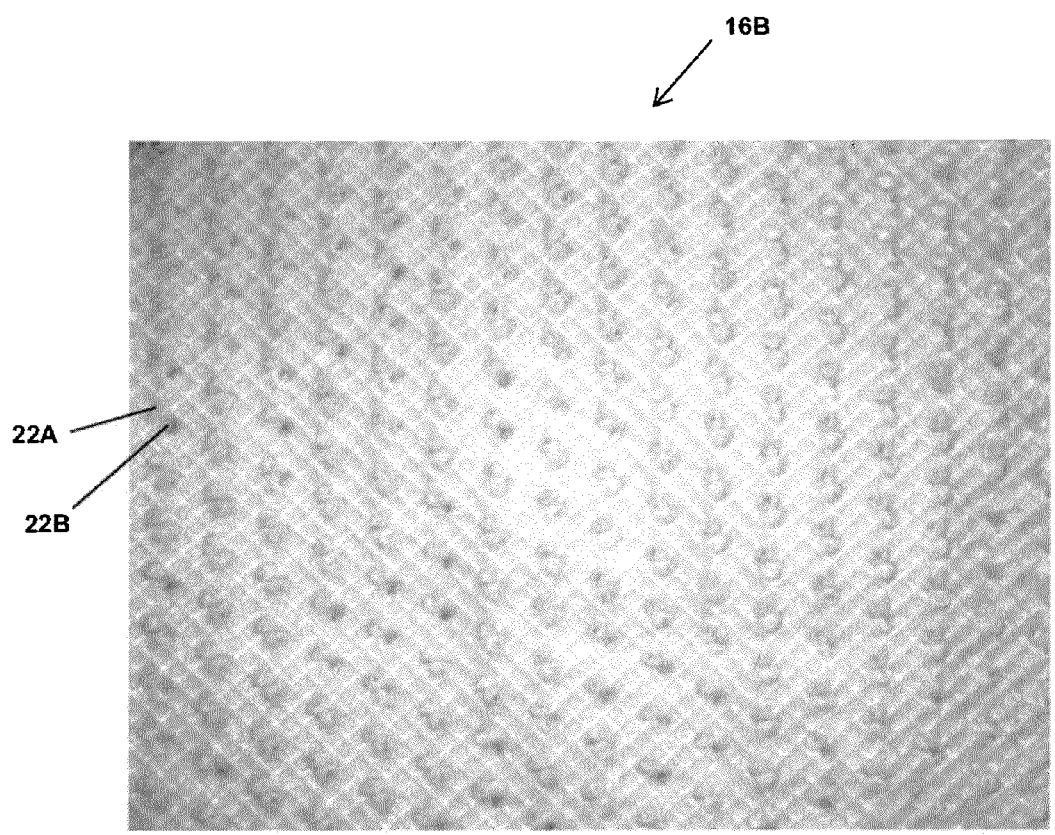
FIG. 8B is a photograph of a second embossed web formed by a process in accordance with an embodiment of the disclosure, illustrating second discrete extended elements in addition to the first discrete extended elements of FIG. 9A.

In both the first and second embossing processes, the compression distance between the compliant substrate 44 and the forming structure 10 is about 0.4 mm. FIG. 8A illustrates the first embossed web 16A formed after performing the first embossing process. The first embossed web 16A includes a plurality of first discrete extended elements 22A with heights of about 90-100 microns. FIG. 8B illustrates the second embossed web 16B formed after performing the second embossing process on the first embossed web 16A. The second embossed web 16B includes a plurality of second discrete extended elements 22B with heights of about 90-100 microns adjacent to the first discrete extended elements 22A. The fine square embossed pattern of the precursor web is still apparent. The second embossing process was performed without controlling the location of the first embossed web 16A as it was fed between the second forming structure 10B and the second pressure source.

Example 2

Embossing Process Using the Different Forming Structures and the Same Pressure Source Embossed webs were produced using first and second forming structures 10A, 10B having the same type of forming elements discrete protruded elements 15. The first forming structure 10A included about 260 protruded elements 15 per square centimeter (a 40 mesh Delrin protruded elements 15 plate). The protruded elements 15 of the first forming structure 10A had a circular cross-section with a diameter of about 150 microns and a center-to-center spacing of about 635 microns. The second forming structure 10B included about 600 protruded elements 15 per square centimeter (a 60 mesh Delrin protruded elements 15 plate). The protruded elements 15 of the second forming structure 10B had a circular cross-section with a diameter of about 150 microns and a center-to-center spacing of about 432 microns. The protruded elements 15 of both the first and second forming structures 10A, 10B have straight sidewalls with a slight inward taper and the tips are rounded. Each of the first and second forming structures 10A, 10B was made of Delrin and had a thickness of about 1.6 mm.

The compliant substrate 44 used as the first and second pressure sources was a two layer rubber laminate obtained from American Roller Company (1440 13$^{th}$ Ave, Union Grove, Wisc., USA, 53182). The base layer is 6 mm thick, made from nitrile rubber and has a Shore A hardness of about 95. The outer layer is 2 mm thick nitrile rubber and has a Shore A hardness of about 65.

The precursor web 34 utilized is the same as that used in Example 1.

Figure 9:
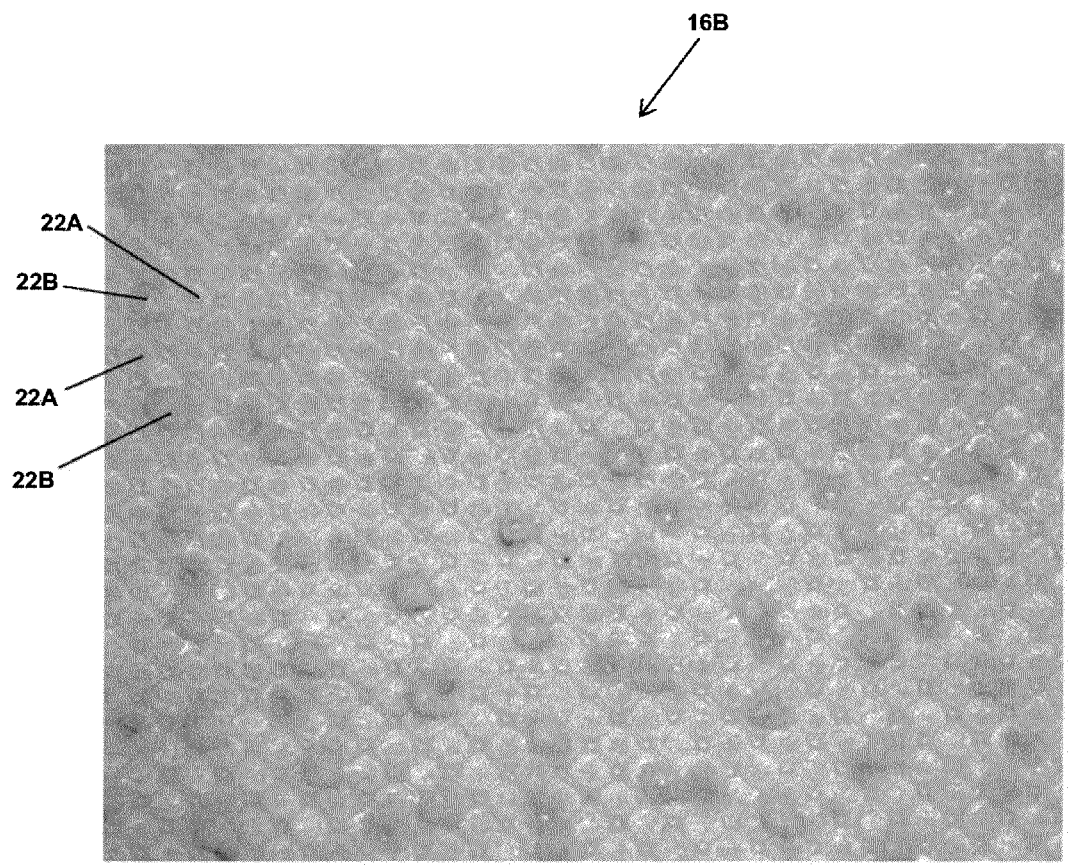
FIG. 9 is a photograph of a second embossed web having first and second discrete extended elements formed by a process in accordance with an embodiment of the disclosure.

The embossing process was performed using a high speed research press at room temperature. The high speed research press is described in detail in U.S. Patent Publication No. 2009/0120308, and is designed to simulate a continuous production line process for embossing the precursor web 34. The press was operated to simulate compliant substrate 44 and forming structure 10 roll diameters of 205 mm. The precursor web 34 was fed between the forming structure 10 and the compliant substrate 44 at a simulated rate of about 7.3 m/sec. In both the first and second embossing processes, the compression distance between the compliant substrate 44 and the forming structure 10 was about 0.4 mm. FIG. 9 illustrates the embossed web 16 resulting from performing the first and second embossing process. The embossed web 16 includes a plurality of first and second discrete extended elements 22A, 22B with heights of about 90-100 microns. As a result of using two different forming structures 10 having different spacing between the apertures 12, the spacing between adjacent first extended elements 22A is larger than the spacing between adjacent second discrete extended elements 22A. The second embossing process was performed without controlling the location of the first embossed web 16A as it was positioned on the second forming structure 10B and the second pressure source.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a polymeric embossed film web, the process comprising:

feeding a precursor polymeric film web between a first pressure source and a first forming structure comprising a plurality of first forming elements;

applying pressure from the first pressure source against the precursor web opposite the first forming structure creating a pressure differential across the precursor web sufficient to conform the precursor web to the first forming elements of the first forming structure, thereby forming a first embossed web comprising a plurality of first discrete extended elements having open proximal ends;

feeding the first embossed web between a second pressure source and a second forming structure comprising a plurality of second forming elements; and applying pressure from the second pressure source against the first embossed web opposite the second forming structure creating a pressure differential across the first embossed web sufficient to conform the first embossed web to the second forming elements of the second forming structure, thereby forming a second embossed web comprising a plurality of second discrete extended having open proximal ends, wherein the first and second forming elements are selected, from the group consisting of discrete protruded elements, discrete apertures, discrete depressions, and combinations thereof, the discrete protruded elements having a height and the discrete apertures and discrete depressions having a depth, the height and the depth being at least substantially equal to a thickness of the precursor web, wherein at least one of the first and second pressure sources is a static gas pressure plenum, and wherein the first and second pressure sources are not velocity pressure sources, and wherein the precursor polymeric film web is free of cellulose.

2. The process of claim 1, wherein at least a portion of the second discrete extended elements are disposed adjacent to the first discrete extended elements.

3. The process of claim 1, wherein the gas comprises a gas selected from the group consisting of nitrogen, carbon dioxide, and mixtures thereof.

4. The process of claim 1, wherein at least one of the first and second pressure source is a compliant substrate.

5. The process of claim 4, wherein the compliant substrate comprises a material selected from the group consisting of elastomers, felts, liquid filled bladders, gas filled bladders, and combinations thereof.

6. The process of claim 1, wherein the first and second pressure sources are the same pressure source.

7. The process of claim 1, wherein the first pressure source is a static pressure plenum and the second pressure source is a compliant substrate.

8. The process of claim 1, wherein the first pressure source is a compliant substrate and the second pressure source is a static pressure plenum.

9. The process of claim 1, wherein the first forming elements and/or the second forming elements have an average edge-to-edge spacing of about 50 microns to about 800 microns.

10. The process of claim 1, wherein the first forming elements comprise discrete protruded elements and the second forming elements comprise at least one of discrete apertures and discrete depressions.

11. The process of claim 1, wherein the first forming elements comprise at least one of discrete apertures and discrete depressions and the second forming elements comprise discrete protruded elements.

12. The process of claim 1, wherein the first and second forming elements comprise discrete protruded elements having substantially the same shape, size, aspect ratio, and edge-to-edge spacing.

13. The process of claim 1, wherein the first and second forming elements comprise discrete protruded elements, and the discrete protruded elements of the first forming elements have at least one of a different shape, different size, different aspect ratio, and different edge-to-edge spacing as the discrete protruded elements of the second forming elements.

14. The process of claim 1, wherein the first and second forming elements comprise at least one of discrete apertures and discrete depressions having substantially the same shape, depth, width, and edge-to-edge spacing.

15. The process of claim 1, wherein the first and second forming elements comprise at least one of discrete apertures and discrete depressions, and at least one of the discrete apertures and discrete depressions of the first forming elements have at least one of a different shape, different depth, different width, and different edge-to-edge spacing as at least one of the discrete apertures and depressions of the second forming elements.

16. The process of claim 1, wherein the first and second forming structures are the same forming structure having the same forming elements.

17. The process of claim 1, comprising applying pressure from the first pressure source for a first dwell time, and applying pressure from the second pressure source for a second dwell time.

18. The process of claim 17, wherein the first and second dwell times are the substantially equal.

19. The process of claim 17, wherein the first and second dwell times are different.

20. The process of claim 1, wherein the temperature of the precursor web and the first embossed web during the process is less than the melting point of the precursor web.

* * * * *